(12) United States Patent
Michelson

(10) Patent No.: US 6,620,163 B1
(45) Date of Patent: Sep. 16, 2003

(54) ANTERIOR CERVICAL PLATING SYSTEM AND BONE SCREW

(76) Inventor: Gary K. Michelson, 438 Sherman Canal, Venice, CA (US) 90291

( * ) Notice: Subject to any disclaimer, the term of this patent is extended or adjusted under 35 U.S.C. 154(b) by 242 days.

(21) Appl. No.: 09/618,036

(22) Filed: Jul. 17, 2000

Related U.S. Application Data

(62) Division of application No. 09/022,293, filed on Feb. 11, 1998, now Pat. No. 6,193,721.
(60) Provisional application No. 60/037,139, filed on Feb. 11, 1997.

(51) Int. Cl.$^7$ ............................................... A61B 17/56
(52) U.S. Cl. ............................ 606/61; 606/69; 606/70; 606/73; 606/76; 606/77; 606/185
(58) Field of Search .............................. 606/60, 61, 69, 606/70, 71, 72, 73, 65, 66

(56) References Cited

U.S. PATENT DOCUMENTS

| | | | |
|---|---|---|---|
| 74,489 A | * | 2/1868 | Bidwell |
| RE31,628 E | | 7/1984 | Allgower et al. |
| 4,488,543 A | | 12/1984 | Tornier |
| 4,493,317 A | | 1/1985 | Klaue |
| 4,651,724 A | | 3/1987 | Berentey et al. |
| 4,794,918 A | | 1/1989 | Wolter |
| 4,959,065 A | | 9/1990 | Arnett et al. |
| 5,019,079 A | | 5/1991 | Ross |
| 5,041,113 A | | 8/1991 | Biedermann et al. |
| 5,053,036 A | | 10/1991 | Perren et al. |
| 5,127,912 A | | 7/1992 | Ray et al. |
| 5,147,361 A | | 9/1992 | Ojima et al. |
| 5,180,381 A | | 1/1993 | Aust et al. |
| 5,190,544 A | | 3/1993 | Chapman et al. |
| 5,234,430 A | | 8/1993 | Huebner |
| 5,300,073 A | | 4/1994 | Ray et al. |
| 5,338,197 A | | 8/1994 | Kwan |
| 5,364,399 A | | 11/1994 | Lowery et al. |
| 5,380,328 A | | 1/1995 | Morgan |
| 5,397,363 A | | 3/1995 | Gelbard |
| 5,423,826 A | | 6/1995 | Coates et al. |
| 5,456,685 A | | 10/1995 | Huebner |
| 5,492,442 A | | 2/1996 | Lasner |
| 5,520,690 A | | 5/1996 | Errico et al. |
| 5,527,314 A | | 6/1996 | Brumfield et al. |
| 5,531,554 A | | 7/1996 | Jeanson et al. |

(List continued on next page.)

FOREIGN PATENT DOCUMENTS

| | | |
|---|---|---|
| DE | 4409833 | 10/1995 |
| DE | 4414781 | 11/1995 |
| WO | WO 94/26193 | 11/1994 |
| WO | WO 95 35067 | 12/1995 |
| WO | WO 96 085206 | 3/1996 |

OTHER PUBLICATIONS

Advertisement for Codman Anterior Cervical Plate System by Codman; Johnson & Johnson; Professional, Inc.; undated.

(List continued on next page.)

*Primary Examiner*—David O. Reip
(74) *Attorney, Agent, or Firm*—Martin & Ferraro, LLP

(57) ABSTRACT

Anatomically contoured anterior cervical plates with bone ingrowth surfaces, providing for intersegmental compressive preloading, and a rigid and locked interface to all of the bone screws, with those engaging the vertebrae deployed in highly convergent pairs. The bone screws have a tapered self-tapping leading end, an increasing root diameter with a generally constant outer diameter with a thread that is narrow and sharp throughout and an enlarged head portion capable of an interference fit to the receiving holes of the plate. Instrumentation consists of plate holders, a compression apparatus and a pilot hole forming device that interlocks with the plate. Methods for spinal compression and bone hole preparation are provided.

239 Claims, 20 Drawing Sheets

U.S. PATENT DOCUMENTS

| | | |
|---|---|---|
| 5,531,746 A | 7/1996 | Errico et al. |
| 5,545,163 A | 8/1996 | Miller et al. |
| 5,545,165 A | 8/1996 | Biedermann et al. |
| 5,549,612 A | 8/1996 | Yapp et al. |
| 5,558,674 A | 9/1996 | Heggeness et al. |
| 5,562,663 A | 10/1996 | Wisnewski et al. |
| 5,578,034 A | 11/1996 | Estes |
| 5,601,553 A | 2/1997 | Trebing et al. |
| 5,607,426 A | 3/1997 | Ralph et al. |
| 5,643,265 A | 7/1997 | Errico et al. |
| 5,662,652 A | 9/1997 | Schafer et al. |
| 5,676,666 A | 10/1997 | Oxland et al. |
| 5,676,703 A | 10/1997 | Gelbard |
| 5,766,254 A | 6/1998 | Gelbard |
| D402,032 S | 12/1998 | Stone |
| D406,646 S | 3/1999 | Stone |
| 5,876,402 A | 3/1999 | Errico |
| 5,876,446 A | 3/1999 | Agrawal et al. |
| 5,954,722 A | 9/1999 | Bono |

OTHER PUBLICATIONS

AESCULAP Scientific Information Booklet; *Anterior Cervical Fusion and Interbody Stabilization with the Trapezial Osteosynthetic Plate Technique* by Wolfhard Casper; 2/86.

Article from Plastic and Reconstructive Surgery; *Comparison of Compression and Torque Measurements of Self–Tapping and Pretapped Screw* by John T. Phillips, M.D., F.R.C.S. (C), and Berton A. Rahn. M.D., D.D.S.; 3/89.

Article from the Journal of Prosthetic Dentistry; *Bone–implant Interface structures after nontapping and tapping insertion of screw–type titanium alloy endosseous implants* by Keiichi Satomi, D.D.S.; Yasumasa Akagawa, D.D.S., Ph.D.; and Hiroshima Tsuru, D.D.S., Ph.D.; 3/88; vol. 59, No. 3.

Brochure by Synthes Spine for *Cervical Spine Locking Plate*; 1991.

ORION Brochure; *Anterior Cervical Plate System, Surgical Technique*, as described by Gary L. Lowery, M.D., Ph.D.; 1996.

CODMAN Brochure; *Anterior Cervical Plate System*; 9/95.

Article from The Surgeon; *The Anterior Plating of the Cervical Spine with the Titanium Hollow Screw System* by E. Morshcer, F. Sutter, H. Jenny and S. Olerud; (1986).

\* cited by examiner

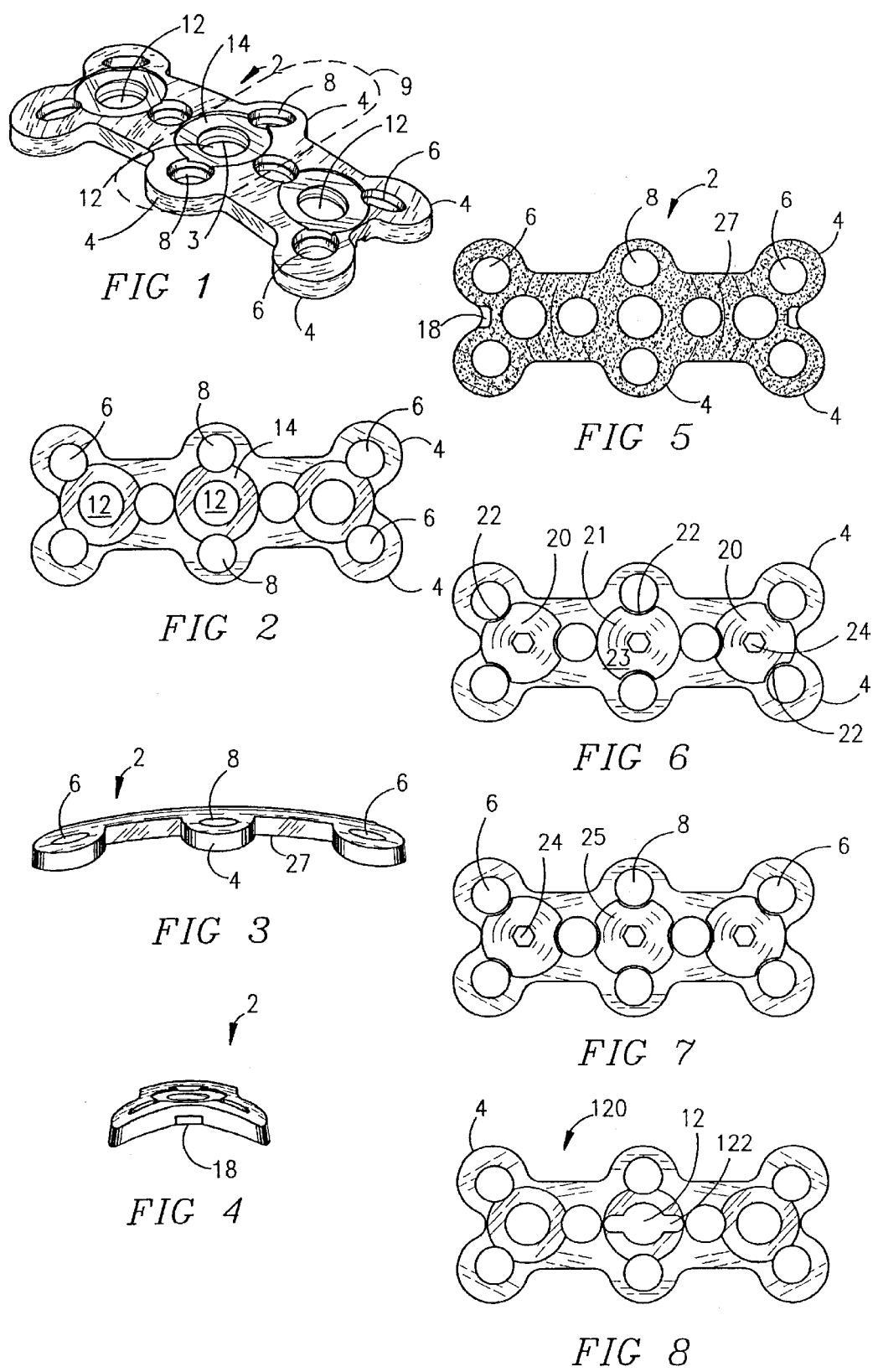

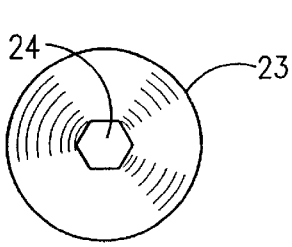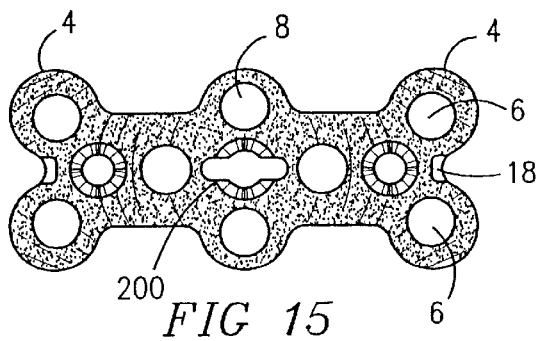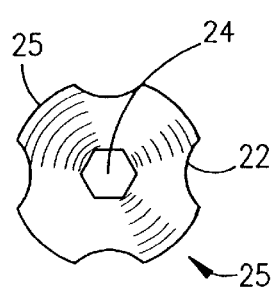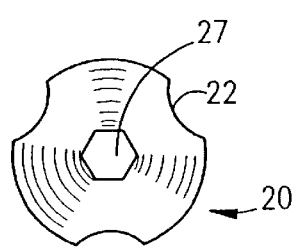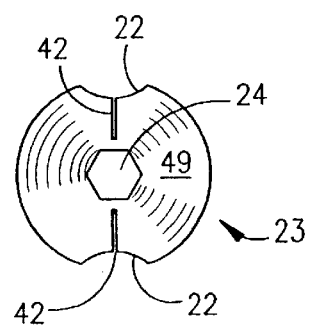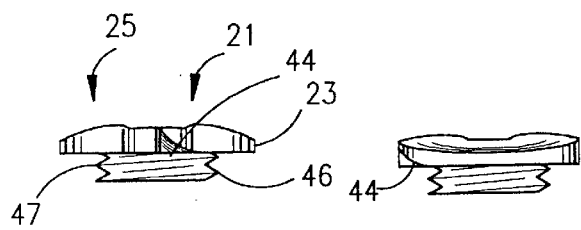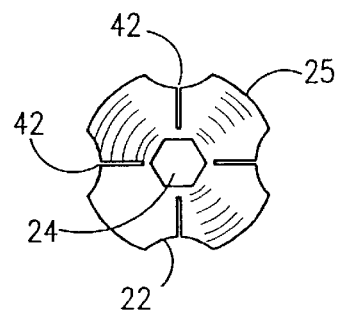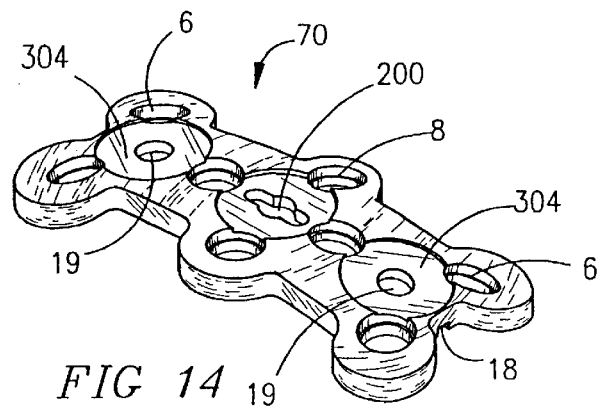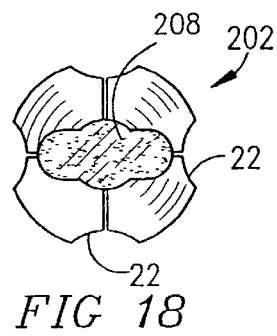

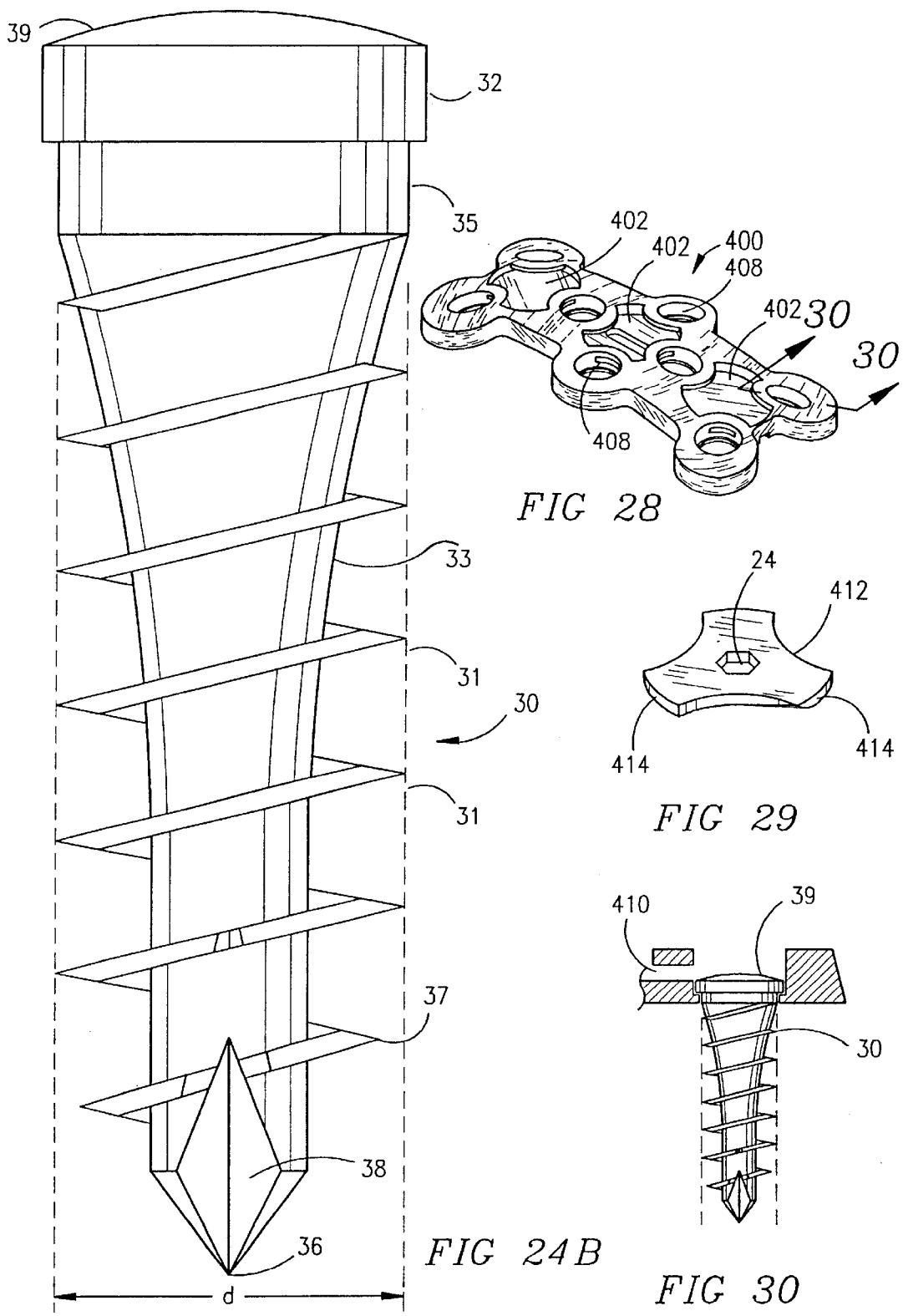

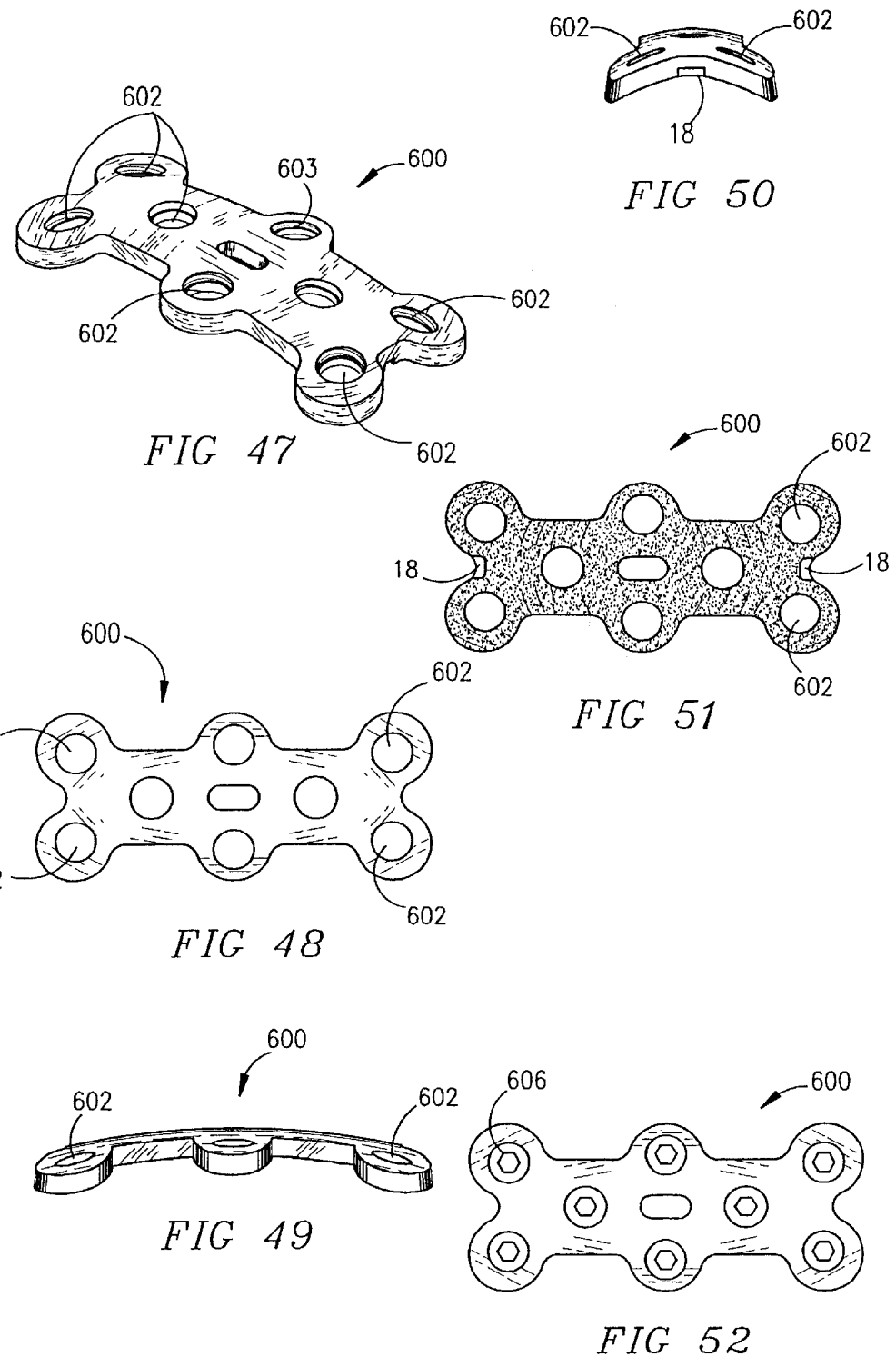

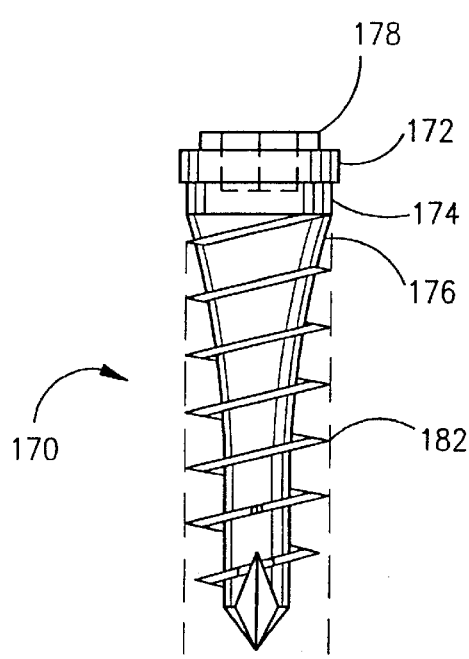
FIG 53
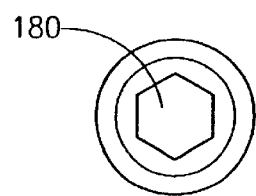
FIG 54
FIG 55
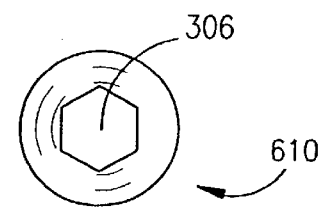
FIG 56
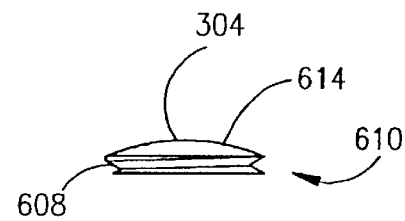
FIG 57
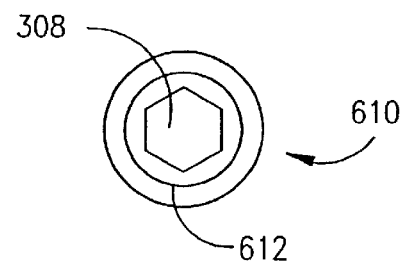
FIG 58
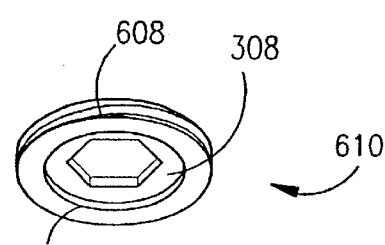
FIG 59

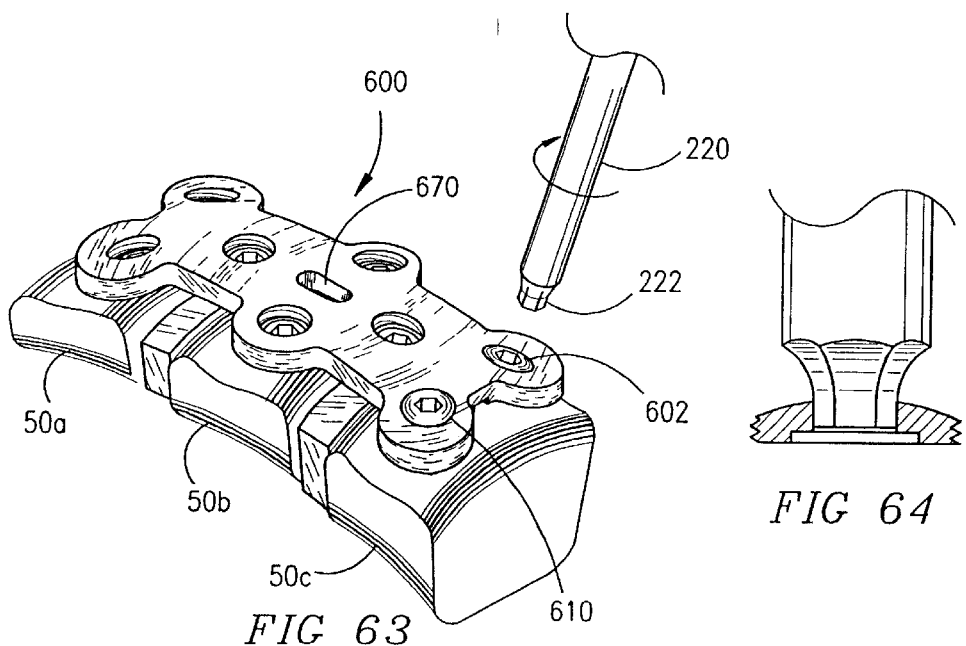
FIG. 63
FIG. 64
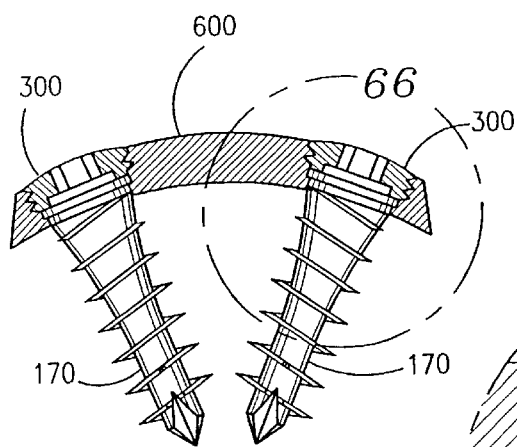
FIG. 65
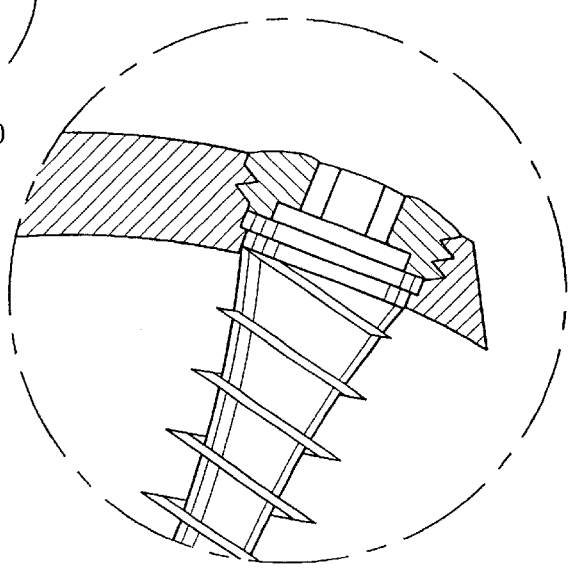
FIG. 66

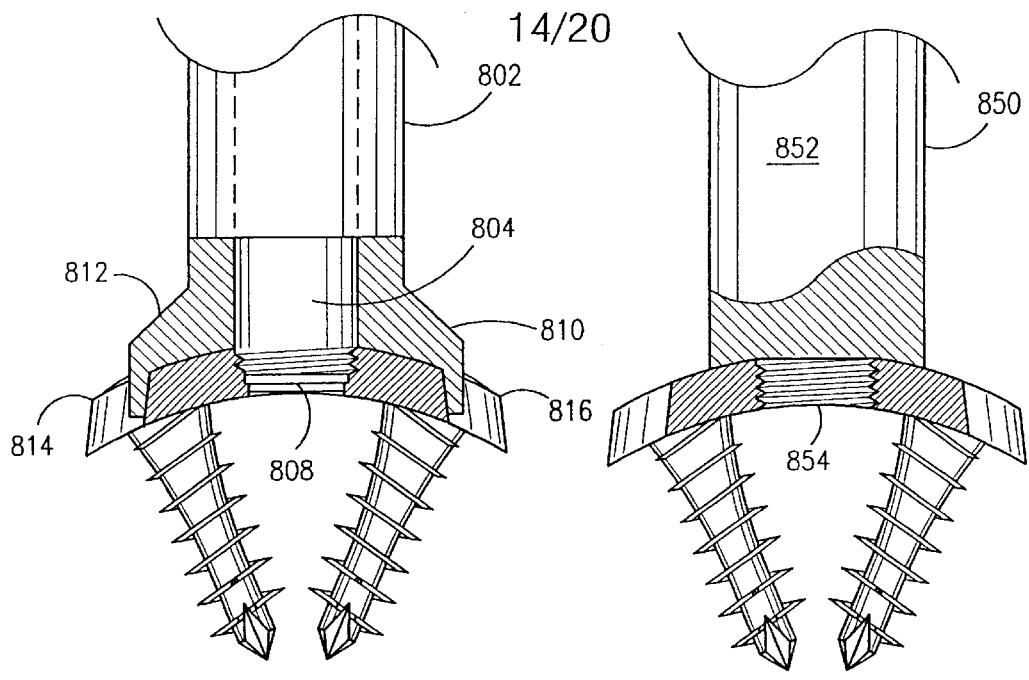
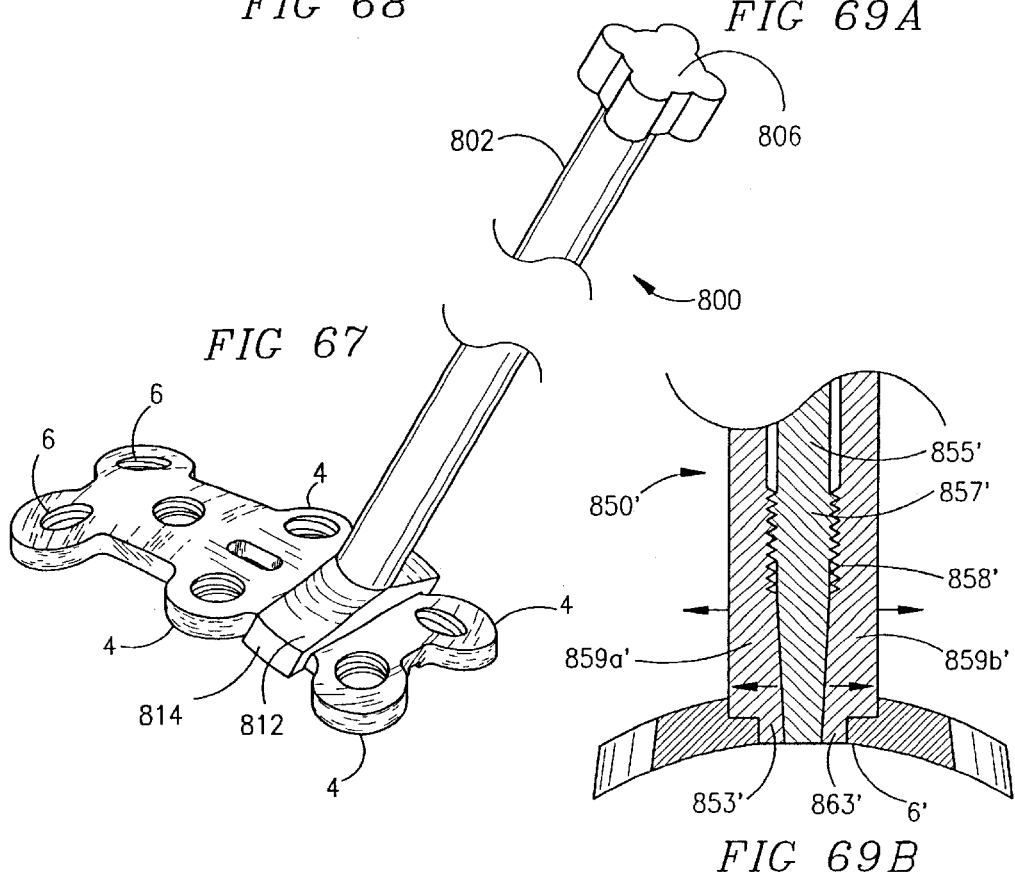

ANTERIOR CERVICAL PLATING SYSTEM AND BONE SCREW

RELATED APPLICATIONS

This is a divisional of application Ser. No. 09/022,293, filed Feb. 11, 1998, now U.S. Pat. No. 6,193,721, and claims the benefit of U.S. provisional application No. 60/037,139 filed Feb. 11, 1997, incorporated herein by reference. Application Ser. No. 09/022,344 filed Feb. 11, 1998, and titled SKELETAL PLATING SYSTEM, now U.S. Pat. No. 6,139,550, is incorporated herein by reference.

BACKGROUND OF THE INVENTION

This is a divisional of application Ser. No. 09/022,293, filed Feb. 11, 1998, and claims the benefit of U.S. provisional application No. 60/037,139 filed Feb. 11,1997, incorporated herein by reference.

1. Field of the Invention

The present invention relates generally to implants, method, and instrumentation for fusion of the human cervical spine from the anterior aspect, and in particular to plate systems for aligning and maintaining adjacent cervical vertebrae in a selected spatial relationship during spinal fusion of those vertebrae.

2. Description of the Related Art

It is current practice in the art to use cervical plating systems for this purpose. Such systems are composed essentially of plates and screws for aligning and holding vertebrae in a desired position relative to one another. The earliest such devices consisted of stainless steel plates and screws and required that the screws passed entirely through the vertebrae and into the spinal canal in order to engage the strong bone tissue (the posterior cortex) of the vertebral bodies. This required the ability to observe or visualize this area radiographically, which is not always possible, especially in the lower cervical spine where the vertebrae may be hidden radiographically by the shoulders.

In order to form holes in the vertebral bodies for insertion of each screw, a drilling operation was performed, followed by a tapping operation. Each of these operations involved the passage of an instrument entirely through the associated vertebral body and into the spinal column. Thus, these instruments come into close proximity.to the spinal cord and the dural sac which are in close proximity to the back surfaces of the vertebral bodies. Any procedure which introduces an object into the spinal canal presents serious risks which are of concern to the surgeon.

The conventional technique of forming a bone screw receiving hole in vertebral bodies by drilling has a number of significant disadvantages. For example, drilling removes bone material, leaving a void and resulting in a loss of bone material. Drilling also causes microfracturing of the bone at the drill bit-bone interface and the resulting fracture lines tend to propagate in directions perpendicular to the wall of the hole. More specifically, the bone material is essentially a type of ceramic which exhibits a brittle pattern of fracture formation and propagation in response to drilling. Furthermore, drilling generates heat which can result in thermal necrosis of the bone material precisely at the interface between the bone and a subsequently installed screw, where necrosis is most harmful. Any bone which does experience necrosis will subsequently be resorbed by the body as part of the bone repair process and this can lead to the loosening of the screw.

Another problem with drilling is that the path of the drill bit is difficult to control and since the drill bit operates by,rotation, it can wind up soft tissue about the associated plate. In addition, unless great care is taken, the drill bit may be driven significantly past the posterior cortex and cause irreparable harm within the spinal canal. Finally, a drill bit may bind and fracture within the vertebral body and can then cause serious injury as the still rotating portion of the drill bit passes into the wound, while the portion of the bit which has broken off may either protrude dangerously from the vertebral body or may be broken off flush with the upper surface of the body so as to be irretrievably embedded therein. In any event, the steps that must be taken to retrieve the broken-off portion of a drill bit will inevitably prolong and complicate the surgical procedure.

In known plating systems, there have been problems with loosening and failure of the hardware, breakage of the screws and plates, and backing but of screws into the patient's throat area. These occurrences generally require further surgical procedures to replace the broken parts or the plates and screws entirely, and to repair any damage that may have been caused.

Other problems which have been encountered with known systems result from the failure of the screws to achieve a sufficient purchase in the bone and the stripping of the screws.

Also, the use of the known plating systems may result in a loss of lordosis, which is the normal curve of the cervical spine when viewed from the side.

Known plating systems additionally experience problems in connection with those procedures where bone grafts are placed between vertebral bodies to achieve an interbody fusion which heals by a process called "creeping substitution". In this process, bone at the interface between the graft and a vertebra is removed by a biological process which involves the production of powerful acids and enzymes, as a prelude to invasion of the interface by living tissue and the deposition, or growth, of new bone. While the plates allow for proper alignment of the vertebrae and their rigid fixation, they can therefore, at the same time unfortunately, hold the vertebrae apart while the resorption phase of the creeping substitution process forms gaps in the bone at the fusion site with the result that the desired fusion does not occur. Such failure is known as pseudoarthrosis. When such a failure occurs, the hardware itself will usually break or become loosened from the spine, thus requiring a further surgical procedure to remove the broken components and another surgical procedure to again attempt fusion.

In response to the problems described above, a second generation of plating.systems has been developed and/or proposed. These include a system disclosed in U.S. Pat. No. 5,364,399 to Lowery and U.S. Pat. No. 5,423,826 to Morscher, as well as cervical spine locking plating systems offered by SYNTHES Spine, the DANEK ORION plate, the CODMAN SHURTLEFF plate, and the SMITH NEPHEW RICHARDS plate, among others. The systems' forming members of this second generation have a number of common properties. They are all made of either a titanium alloy or pure titanium rather than stainless steel, to minimize adverse tissue reactions and are MRI compatible, which stainless steel is not. The screws and the plates have been given increased thickness in order to achieve increased strength. The screws have larger diameters to improve their purchase without requiring that they engage the posterior cortex of the vertebral bodies. Some mild longitudinal contouring of the plates is employed to allow for some lordosis, and/or limited transverse contouring to better follow the generally curved aspect of the front of the vertebral bodies. Mechanisms are employed for securing the vertebral bone screws to their associated plates in a manner to prevent the screws from backing out. While this second generation of plating systems represents a significant improvement over earlier systems, certain existing problems persist, while new problems have been created.

For example, since the screws no longer extend into the posterior cortex, it is common for the threads in the tapped screw hole to become stripped and for the screws to fail to gain a suitable purchase. In addition, screw breakage continues to be experienced and occurs most commonly at the junction of the screw to the posterior aspect of the plate. The screws employed in both the SYNTHES system and the SMITH NEPHEW RICHARDS system are particularly vulnerable to this problem because those screws are hollow at the level where they attach to the plate to permit the internal reception of locking screws.

In an attempt to prevent screw to plate junction breakage of the screw, more recent designs of screws have an increasing root diameter from tip to head, which thus far has resulted in a near useless stubby and blunt thread near the screw head with little holding power and little tactile feedback to the surgeon to signal the completion of tightening prior to stripping of the screw within the bone. Based on empiric studies testing these prior art screws, the use of a pretapped hole, rather than a self-tapping screw, was found to be preferred for pullout strength and thus these screws have not been self-tapping and thus the screw holes must be pre-tapped. Since the thread cutting portion of a tap is necessarily sharp and rotated to work, there is a serious risk of damage to the surrounding soft tissues when it is used. This is compounded by the fact that the plates employed in these systems do not provide sufficient long axis contouring to make full allowance for lordosis and do not have sufficient transverse contouring to prevent rocking of the plate about its longitudinal axis and to conform to the anterior shape of the vertebral bodies, so that these plates do not prevent soft tissue from creeping in from the sides and beneath the screw holes thus exposing these tissues to damage by the drill and the tap. While it is possible, at the time of surgery, to make some change in the contouring of these plates, this is generally limited to contouring of the longitudinal axis and quite often causes distortion of the plate's bone screw holes and screw hole to plate junctions in a manner which has an adverse effect on the screw-plate interlock. Lack of proper contouring prevents these plates from having an optimally low profile relative to the spine.

In some of the second generation cervical plating systems, screw backout continues to occur, because these plates could not be designed to allow for the locking of all of the screws. Specifically, while the designers of these plates recognized the importance of securing the bone screws to the plates, they were unable to lock all of the screws and had to settle for leaving some of the screws unlocked.

Furthermore, several of these second generation systems utilize tiny and delicate "watchmaker" parts to achieve interlocking. These parts are characterized by the need to engage them with particularly delicate small ended screw drivers. These interlocking components are easily rendered ineffective by any effort to alter the contours of a plate during surgery.

Despite the improvement of these second generation plating systems over the first problems, the problems still persist, the most important of which is pseudoarthroses, and particularly "distraction pseudoarthroses". Although these second generation plates have clearly led to an increase in fusion rate, when a failure to produce fusion occurs, it is generally accompanied by bone resorption along a line at the graft-to-vertebra junction, which can be seen on a radiograph.

In the case of the weak first generation plates and screws, the plates might hold the vertebrae apart, preventing fusion, but only until the hardware would break, relieving the distraction, and then allowing the fusion to occur. The second generation systems of plates are too strong to allow this to occur, thus requiring further surgical procedures for the correction of the pseudoarthroses.

Compression plates are well-known and are widely used in orthopedic surgery for the stabilization of tubular bones, and sometimes also flat bones. Such plates may rely on some external compression means or may be self-compressing, relying on the ability of the screw head to slide within a ramped slot such that the tightening of the bone screws through the plate imparts a linear motion perpendicular to the screw axes. U.S. Pat. No. 5,180,381 discloses an attempt to employ such a mechanism in connection with anterior spinal fixation.

However, it has been found that all of the proposed self-compressing plating systems have in common the need for a screw to engage both a proximal and a distal cortex, (bone casing of very dense bone material), so as to anchor the screw tip in a manner to allow the plate to move relative to the screw when tightened rather than allowing the plate to drag the screw off axis. However, as already discussed earlier herein, when a screw is to engage the posterior cortex of the vertebral body, it is necessary for the drill and the tap which form the screw hole, as well as the screw tip itself, to all enter the spinal canal, thereby exposing the spinal cord to damage.

While the system disclosed in U.S. Pat. No. 5,180,381 avoids such danger by engaging the vertebral body end plate instead of the posterior vertebral body cortex, the path of the screw is of necessity quite short, so that there is very little opportunity for the screw threads to achieve additional purchase within the vertebral body. It would therefore appear that to the extent that the device disclosed in U.S. Pat. No. 5,180,380 is able to achieve its stated objectives, it would pull the front of the spine together more than the back and would not appear to compress the back of the vertebral bodies at all, thus producing an undesirable iatrogenic loss of the normal cervical lordosis. Such a situation is disruptive to the normal biomechanics of the cervical spine and potentially quite harmful.

The creation of compression between adjacent vertebrae would offer a number of advantages, including reduced distraction pseudoarthrosis, increased surface area of contact between the graft and vertebrae as slightly incongruent surfaces are forced together, increased osteogenic stimulation, since compressive loads stimulate bone formation, and increased fusion graft and spinal segment stability.

Among the new problems created by these second generation systems is a tendency for the small "watchmaker" parts used to lock the bone screws to the plate to fall off of the driver used for attaching those parts, or out of the associated plates and to become lost in the wound. In addition, these small parts are quite fragile and require specialized additional instruments for their insertion and/or manipulation. Furthermore, incorrect bone screw placement relative to the axis of a plate hole may render the screw locking mechanism unworkable or may cause sharp and jagged shavings of titanium to be formed as a locking screw is driven into contact with an improperly seated bone screw. The means for establishing bone screw to plate hole alignment and preparation are less than reliable. Furthermore, most of these second generation systems lack a reliable and effective means for positioning and holding the plate during attachment.

Specific features of various prior art systems will be summarized below.

The system disclosed in U.S. Pat. Nos. 5,364,399 and 5,423,826, cited earlier herein, includes a thin stainless steel plate which allows for side-by-side or offset bicortical screw placement, the plate having a combination of screw holes and slots.

The "Acromed" system includes a titanium plate and screws which require bicortical screw placement. This system does not include any locking means for the bone screws.

The system disclosed in U.S. Pat. No. 5,180,381 includes an "H" shaped plate having a combination of ramped slots and a hole which requires bicortical screw placement at a 45° angle to the plane of the plate. This patent discloses that this angular positioning is for the purpose of producing compression.

The SYNTHES Morscher plate system employs hollow, slotted screw heads. The screws are placed unicortically so that the heads, when properly aligned, come to rest in the upper portion of the plate holes. The upper portion of each screw is internally threaded to receive a tiny screw which is screwed into the bone screw head in order to increase the interference fit between the bone screw head and the wall of the associated plate hole.

In the system disclosed in U.S. Pat. Nos. 5,364,399 and 5,423,826, use is made of pairs of unicortical bone screws that may be locked in place at both ends of the associated plate by locking screws which have a small diameter shank and a large head. At each end of a plate two bone screws may be locked in place by a single locking screw which is situated between the bone screws. Generally, the plate is provided, between its two ends, with a diagonal slot or slots for receiving one or more additional screws, each additional screw being securable in a bone graft or a respective vertebra which is spanned by the plate. There is no locking screw associated with these intermediate bone screws to lock the bone screws to the plate.

The Codman Shurtleff plating system utilizes the side of a preinstalled rivet having a head rotatable to press against the side of the head of a bone screw so as to secure that one screw to the plate. The plates of this system also are provided with holes for receiving intermediate screws, but these screws are not associated with any locking means.

While the designers of the last-mentioned systems recognized the importance of locking the bone screws in position on their associated plates, they did not provide for any locking of the intermediate bone screws in their associated holes.

In an earlier version of the Codman Shurtleff system, the locking mechanism was a lever pivotable about a shaft passing entirely through the plate and then flared so as to retain the shaft within the plate. The lever was rotated after the bone screw had been inserted to engage the head of the bone screw and thus secure the bone screw to the plate.

Based on a consideration of the features of all of the known cervical plating systems, it appears that there remains a need for an improved system having the following combination of features:

1) The plate should be sufficiently strong to perform its intended function without mechanical failure;
2) The plate should be preformed in three dimensions so as to anatomically conform in both the longitudinal and transverse planes to the anterior cervical spine;
3) The plate should be constructed so that all of the bone screws are generally perpendicular to the plate when viewed from the side, but pairs of screws are highly convergent corresponding to any vertebral level when viewed from the bottom, or on end;
4) Each pair of screws engages in a respective vertebra and the high convergence of screws in a pair allows the length of the screws which engage the bone to be longer and still remain within that vertebra and provide a safer and stronger engagement with the vertebrae;
5) The system should include bone screws which are capable of achieving enhanced purchase within the bone of the vertebral body and without the need to penetrate the posterior vertebral cortex and enter the spinal canal;
6) Use should be made of a screw which is self-tapping, thereby eliminating the need for separate tapping steps;
7) A reliable means should be provided for engaging and manipulating the plate during installation;
8) The plate should be engageable with an instrument means which can reliably produce bone screw holes which are coaxial with the screw holes in the plate;
9) It should be possible to prepare the vertebral bone to receive the bone screws so as to produce a stronger connection and a reduced danger of thread stripping by means of a pilot hole punch creating a pilot hole for the bone screws;
10) Alternatively to the use of a pilot hole punch, a relatively (compared to the overall root diameter of the screw) small diameter drill may be used to create the pilot hole.
11) Means should be provided for locking each and every bone screw in position relative to the plate, and the locking means should be of sufficient size and strength to reliably perform its intended functions;
12) Bone screw locking means should preferably be retainable by the plate prior to bone screw insertion, or should be reliably attachable to a driver to prevent any small parts from becoming loose in the wound; and
13) The system should be capable of effecting compression of the vertebral segments to be fused while maintaining and/or restoring lordosis.

OBJECTS OF THE INVENTION

It is an object of the present invention to provide an improved anterior cervical plating system, installation instrumentation, and installation method which has the above described features and which avoids many of the shortcomings of previously known systems.

One object of the present invention is to provide a locking mechanism where a plurality of bone screws used for attaching the plate to the vertebrae can be easily and reliably locked in place at the same time by a single operation.

Another object of the present invention is to provide a vertebral plate in which the locking mechanisms for locking the bone screws may be pre-installed by the manufacturer prior to the insertion of the bone screws by the physician so that the physician does not have to attach the locking mechanism to the plate as a separate procedure during the operation.

Another object of the invention is to provide an anterior cervical plating system which allows for the intersegmental compression of the spinal segment (compression of the adjacent vertebrae and the fusion graft in the disc space between the adjacent vertebrae) in lordosis, and similarly, where desired, multisegmental compression.

A further object of the invention is to provide bone screws which provide for tactile feedback to the surgeon to assure sufficient tightening of the screws while avoiding stripping and are less prone to failure by breakage or by loosening.

Another object of the invention is to provide bone screws which achieve optimal purchase within the bone, without the need to penetrate the posterior cortex of the vertebrae.

A further object of the invention is to provide plates which are textured or otherwise treated to promote bone growth from vertebrae to vertebra beneath the plate.

Another object of the invention is to provide a plate which is constructed to reliably engage an instrument for forming all bone screw holes coaxial with the holes formed in the plate, the instrument having integral depth limiting means which completely eliminates the danger of perforation of the posterior vertebral wall or entry into the spinal canal.

Yet another object of the invention is to provide a system in which the bone screws and locking mechanisms, when fully installed, have a low profile.

It is another object of the present invention to provide for an anterior cervical plating system which is at least in part bioresorbable.

It is another object of the present invention to provide for an anterior cervical plating system comprising at least in part of bone ingrowth materials and surfaces.

It is another object of the present invention to provide for an anterior cervical plating system comprising at least in part of bone growth promoting substances.

It is another object of the present invention to provide instruments for reliably and easily performing the installation of the plates of the present invention.

It is still another object of the present invention to provide an improved method of installing the plates of the present invention.

The above and other objects and features of the invention will become more readily apparent from the following description of preferred embodiments of the invention, provided with reference to the accompanying drawings, which illustrate embodiments of the invention solely by way of non-limiting example.

SUMMARY OF THE INVENTION

The plating system of the first preferred embodiment of the present invention comprises a plate having a length sufficient to span a disc space and to overlap, at least in part, at least two adjacent cervical vertebrae, a substantial portion of the lower surface of the plate preferably being bi-concave, that is concave curved along a substantial portion of the longitudinal axis of the plate and concave curved along a substantial portion of the transverse axis of the plate. The lower surface of the plate may also textured and/or treated to induce bone growth along the lower surface of the plate which contacts the cervical vertebrae. The plate is provided with a plurality of bone screw receiving holes which extend through the plate, from the upper surface to the lower surface of the plate, and at least one locking element is associated with the bone screw receiving hole. The plate and its component parts, may be made of any implant quality material suitable for use in the human body, and the plate and associated component may be made of a bioresorbable material.

Bone screws are each insertable into a respective bone screw receiving hole for attaching the plate to a vertebra. A locking element, is engageable to a locking element receiving recess and has a head formed to lock the bone screws to the plate. In the preferred embodiment a single locking element locks a number of different bone screws in place. The locking elements are pre-installed prior to use by the surgeon in a manner so as to not impede installation of the bone screws.

As a&result, the problems previously associated with the locking screws of the type applied after the insertion of the bone screws, including the problems of instrumentation to position and deliver to the plate the locking means, backing out, breakage, stripping and misthreading associated with the prior art more delicate locking screws resembling "watchmaker's parts", are eliminated.

In an alternative embodiment of the present invention, a locking element fits within a respective bone screw receiving hole to lock a respective one of the bone screws in place. According to this second embodiment of the invention, each of the bone screws is locked to the plate by means of an individual locking element which bears against at least a portion of the bone screw. Since no other holes need be formed in the plate to attach the locks to the plate, the plate remains quite strong.

The locking elements can be in many forms to achieve their intended purpose, such as, but not limited to, screws, threaded caps, rivets, set screws, projecting elements, and the like.

Also, a novel bone screw is disclosed so as to prevent pulling out of the bone screw during use. This is achieved by a design which includes a screw in.which the outer diameter or crest diameter of the thread is maintained substantially constant along the entire length of the shaft of the bone screw, from below the head to above the tip, where threads of a lesser outer diameter facilitate insertion. The screw tip is fluted at its distal end to be self-tapping. The thread also has an extremely thin and sharp profile to cut into and preserve the integrity of the vertebral bone stock.

The plating system does not require that the head of the bone screw be hollow, or that additional holes be placed through the plate in addition to those provided for the passage of the bone screws. It will be appreciated that bone screws are weakened when their heads are hollow and that plates are weakened when they are provided with additional holes.

Additionally, the plate of the disclosed systems permit the proper aligning of the holes in the plate for the bone screws and for the plate to be easily applied to the vertebrae in compression. The plates include appropriate slots and engagement means for engaging compression instrumentation, described in detail below, for applying a compression force between adjacent vertebrae to which the plate is attached, in a reliable and easy manner.

An improved locking screw driver is provided. The driver provides for a wedged interference fit with a recess in the head of the bone screws and the head of the locking elements. The same driver is usable for both bone screws and locking elements. The driver ensures that the locking element cannot fall off the driver and become lost in the wound. The driver has a tapered end to facilitate insertion into the complimentary recess in the head of the screws and is used to engage and pick up the locking elements. Alternatively, the receiving socket can be tapered to the same purpose.

Alternatively, a combination bone screw and locking screw driver is disclosed in which the bone screw driver passes through a longitudinal opening in the locking screw driver so that both the bone screw and the locking screw can be loaded prior to insertion of the bone screw and both can be tightened with one instrument, without removing it from position.

Also, instruments are provided for forming pilot holes to assist in the ease and accuracy of the installment of the bone screws, and for creating a creating a compression force between adjacent vertebrae during installation of the plate and for holding the plate during installation.

BRIEF DESCRIPTION OF THE DRAWINGS

FIG. 1 is a top perspective view of a first embodiment of a cervical spine multiple locking plate.

FIG. 2 is a top plan view of the cervical spine multiple locking plate shown in FIG. 1.

FIG. 3 is a side elevational view of the cervical spine multiple locking plate shown in FIG. 1.

FIG. 4 is an end view of the cervical spine multiple locking plate shown in FIG. 1.

FIG. 5 is a bottom plan view of the cervical spine multiple locking plate shown in FIG. 1.

FIG. 6 is a top plan view of the cervical spine multiple locking plate shown in FIGS. 1–5, with locking elements installed in an open configuration.

FIG. 7 is a top plan view of a modification of the plate of FIGS. 1–6 with a four bone screw locking element in place.

FIG. 8 is a top plan view of a further embodiment of a cervical locking plate of FIG. 1 with an elongated central slot for increased compression capability.

FIG. 9 is a top plan view of a locking element for use with the plates of FIGS. 1–6.

FIG. 10 is a top plan view of a locking element for use with the central opening of the plate of FIGS. 7 and 22.

FIG. 11 is a top plan view of a locking cap for use in the end openings shown in FIGS. 1, 6, and 7.

FIG. 12 is a side elevational view of the locking element of FIG. 16.

FIG. 13 is a side elevational view of another embodiment of the locking element of FIG. 16.

FIG. 14 is a top perspective view of an alternative embodiment of cervical spine multiple locking plate for use with locking rivets.

FIG. 15 is a bottom plan view of the cervical spine multiple locking plate of FIG. 14.

FIG. 16 is a top plan view of a two bone screw locking element.

FIG. 17 is a top plan view of an alternative embodiment of a four bone screw locking element having head slits for increased flexibility of the locking tabs.

FIG. 18 is a bottom plan view of a rivet type locking element for use with the central opening of the plate of FIG. 14.

FIG. 24B is an enlarged side elevational view of the bone screw of FIG. 24A.

FIG. 28 is a top perspective view of a fourth embodiment of a cervical spine multiple locking plate.

FIG. 29 is a top perspective view of a locking element for use with the plate of FIG. 28.

FIG. 30 is a partial side sectional view of the plate of FIG. 28 along lines 30—30 with a bone screw in place.

FIG. 47 is a top perspective view of a first embodiment of a single locking plate.

FIG. 48 is a top plan view of the plate shown in FIG. 47.

FIG. 49 is a side elevational view of the plate shown in FIG. 47.

FIG. 50 is an end view of the plate shown in FIG. 47.

FIG. 51 is a bottom plan view of the plate shown in FIG. 47.

FIG. 52 is a top plan view of the plate shown in FIG. 47, with locking elements in place.

FIG. 53 is a side elevational view of a bone screw used with the plate shown in FIG. 47.

FIG. 54 is a top end view of the bone screw shown in FIG. 53.

FIG. 55 is a bottom end view of the bone screw of FIG. 53.

FIG. 56 is a top plan view of a locking cap for use with the single locking plate of FIG. 47.

FIG. 57 is a side elevational view of the locking cap shown in FIG. 56.

FIG. 58 is a bottom plan view of the locking cap shown in FIGS. 56 and 57.

FIG. 59 is a bottom perspective view of the locking cap of FIGS. 56–58.

FIG. 63 is a top perspective view of a single locking plate installed along a segment of the spine with two locking caps installed in two bone screw receiving holes.

FIG. 64 is a side elevational view in partial cross section of a locking cap engaged to a driver for installing the locking cap.

FIG. 65 is a partial cross sectional view of the plate, bone screws and locking caps along line 65—65 of FIG. 63.

FIG. 66 is an enlarged fragmentary view of area 66 of FIG. 65.

FIG. 67 is a perspective view of a cervical locking plate being held by an alternative plate holder instrument.

FIG. 68 is an end sectional view showing the plate holder of FIG. 67 engaging a plate.

FIG. 69A is an end sectional view of an alternative embodiment of the plate holder.

FIG. 69B is an end sectional view of another alternative embodiment of the plate holder.

DETAILED DESCRIPTION OF THE DRAWINGS

Figure 19:
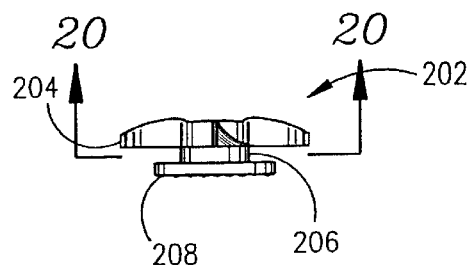
FIG. 19 is a side elevational view of a rivet locking element.

The present invention will be described first in association with the preferred embodiment of the plate system in which a plurality of bone screws are locked in place with one locking element. This is referred to as the multiple locking plate system. The multiple locking plates will be described, then the locking elements for locking the bone screws to the plate, then the bone screws associated with the multiple locking plates, and finally the instrumentation and method of installation of the multiple locking plates. Thereafter the plate systems in which a single locking element locks a single bone screw will be described. This is referred to as the single locking plate system. The locking elements, bone screws, instrumentation, and method of installation associated with the single locking plate will then be discussed.

1. Multiple Locking Plate System.

The preferred embodiment of the multiple locking anterior cervical locking plate 2 according to the present invention (here shown by way of example for use in a two level fusion (three adjacent vertebrae)) is shown in FIGS. 1–5. Plate 2 has a generally elongated form whose outline generally departs from rectangular due to the presence of lobes or lateral projections 4 at the corners and at the center of the sides of plate 2. Each lobe 4 has a rounded outline and contains a respective circular bone screw receiving hole 6. Two additional intermediate circular bone screw receiving holes 8 are located inwardly of the sides of plate 2 and are centered on the longitudinal center line of plate 2. Lobes 4 give plate 2 additional strength in the region surrounding each bone screw receiving hole 6. It is recognized that other shapes for the plate 2 may be employed.

The intermediate paired bone screw receiving holes 8 are for use with a two level (three vertebrae) fusion The intermediate bone screw receiving holes 8 may be eliminated for a single level (two vertebrae) fusion, or additional intermediate bone screw receiving holes 8 may be added if additional levels are to be, fused.

Plate 2 is further provided with three locking element holes 12, each of which in the preferred embodiment is internally threaded 3, and each of which is surrounded by a shallow countersunk region 14. As will be described in greater detail below, in the preferred embodiment, bone screws are inserted in the bone screw receiving holes and a single pre-installed locking element associated with each of the locking element holes 12 locks a number of bone screws 30 in position at one time.

The number of paired bone.screw holes generally correspond to the number of vertebrae to be fused. A plate for a one level fusion could have but a single locking element hole 12, while plates for fusing more than two levels (three vertebrae) could have additional middle locking element holes 12 corresponding to additional paired bone screw holes. In the embodiment illustrated in FIGS. 1–6, each end locking element 20 will lock three bone screws 30 in place, while the locking screw 21 in the central locking hole 12 locks two bone screws 30 in place. As shown in FIG. 7, central locking element 25 can also be configured so that four bone screws 30 are locked at one time.

As shown particularly in FIGS. 3, 4 and 5, plate 2 is shaped so that its bottom surface 27 (the surface which will be in contact with the vertebral bodies) has a bi-concave curvature, being concave both in the longitudinal plane (corresponding to its length) and in the plane transverse thereto, corresponding to its width. The concave curvature in the longitudinal plane conforms to the proper shape of the anterior aspect of the spine with the vertebrae aligned in appropriate lordosis. That longitudinal curve is an arc along the circumference of a circle (referred to herein as the "radius of curvature") 15.0 cm to 30.0 cm in radius and more preferably 20.0–25.0 cm in radius. Viewed on end in FIG. 4, the plate 2 has a radius of curvature of a circle 15–25 mm in radius, but preferably 19–21 mm in radius. While the plate 2 may have a thickness between 2 to 3 mm, a thickness of between 2.25 and 2.5 mm is preferred.

Having the bottom surface 27 of plate 2 contoured so that it is able to lie flush against the associated vertebral bodies is in contrast to conventional plates which have larger radii of curvature that contact the vertebral bodies only along the longitudinal centerline of the plate, thereby permitting side-to-side rocking of the plate relative to the vertebral bodies. The contour of the plate of the present invention provides effective resistance to rocking of the plate 2 relative to the vertebral bodies about the longitudinal center line of the plate, thereby reducing stress on the plate 2 and bone screws 30, and preventing the soft tissues from becoming engaged beneath the plate.

Other advantages produced by the above curvature are that the plate 2 will conform more closely to the facing bone surface; the plate 2 will project from the spine by a smaller distance; soft tissue will be prevented from sliding underneath the edges of the plate 2, where it could be subject to damage; and the angle of the bones crews 30, perpendicular to the plate when viewed from the side, when installed will be at a substantial converging angle, trapping the vertebral bone between the bone screws 30, and thus more strongly anchoring the plate to the spine.

As shown in FIG. 5; the bottom surface 27 of plate 2, preferably has a porous, roughened, and/or textured surface layer and may be coated with, impregnated with, or comprise of fusion promoting substances (such as bone morphogenetic proteins) so as to encourage the growth of bone along the underside of the plate 2 from vertebrae to vertebrae. The textured bottom surface 27 also provides a medium for retaining fusion promoting substances with which the bottom surface 27 layer can be impregnated prior to installation. The bottom surface 27 of plate 2 may be given the desired porous textured form by rough blasting or any other conventional technology, such as etching, plasma-spraying, sintering, and casting for example. If porous, the bottom surface 27 is formed to have a porosity or pore size in the order of 50–500 microns, and preferably 100–300 microns. Fusion promoting substances with which the porous, textured bottom surface 27 can be impregnated include, but are not limited to, bone morphogenetic proteins, hydroxyapatite, or hydroxyapatite tricalcium phosphate. The plate 2 may comprise of at least in part a resorbable material which can further be impregnated with the bone growth material so that as the plate 2 is resorbed by the body of the patient, the bone growth material is released, thus acting as a time release mechanism. Having the plate 2 being made from a material that is resorbable and having bone growth promoting material present permits the vertebrae to be fused in a more natural manner as the plate becomes progressively less load bearing thereby avoiding late stress shielding of the spine.

Figure 36:
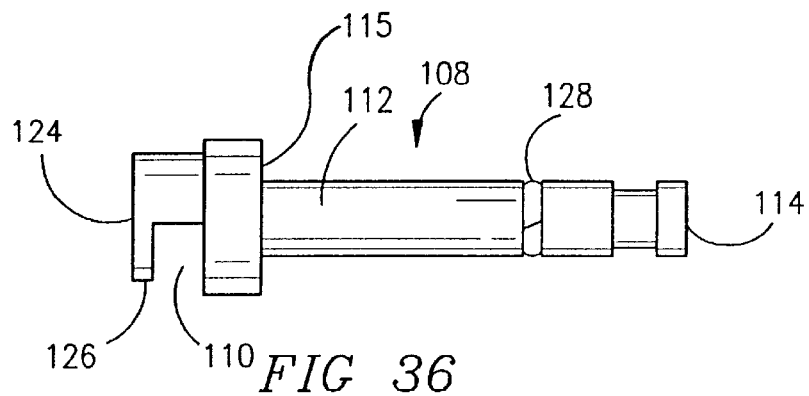
FIG. 36 is a side elevational view of a plate engaging hook for use with the compression apparatus shown in FIG. 38.

As further shown in FIGS. 4 and 5, at least one end of plate 2 has a recess 18 that can cooperate with a compression apparatus, described in detail later in reference to FIGS. 36 and 38.

FIG. 6 is a top plan view of the plate 2 of FIG. 1 with locking elements 20, 21 inserted into the locking element receiving holes. In the preferred embodiment, the locking elements 20, 21 are in the form of screws that cooperate with the threaded interior 3 of the locking holes 12. Each of these locking elements 20, 21 is shown in its initial open orientation, where the orientation of the cutouts 22 in the head 23 of each locking element 20, 21 is oriented so as to permit introduction of bone screws 30 into adjacent bone screw receiving holes 6, 8 without interference by the head 23 of the locking element 20, 21. It is appreciated that other configurations of the head 23 are possible so as to permit introduction of bone screw into adjacent bone screw receiving holes without interference by the head 23.

FIG. 8 is a top view of another embodiment of plate 2 of FIGS. 1–5, and is generally referred to as plate 120. Plate 120 is provided with a longitudinally extending elongated slot 122 along its longitudinal axis which is superimposed on the middle locking hole 12. Elongated slot 122 allows additional relative movement between plate 120 and a compression post 54 associated with a compression tool during the compression procedure, as discussed below.

Referring to FIGS. 14 and 15, an alternative embodiment of a multiple locking plate referred to by the number 70 is shown. In plate 70, rather than the threaded locking hole 12, a central opening 200 for receiving a removable rivet 202, of the type shown in FIGS. 17–20, is provided. FIG. 15 is a bottom plan view of the plate 70 shown in FIG. 14. The contour of the plate 70 is the same as that of the plate 2 shown in FIGS. 1–5. The rivet 202 is removable and fits within the unthreaded opening 200, comparable to the locking hole 12 and slot 122 described above. Other embodiments may employ a rivet that is not removable, but is manufactured as part of the plate 70 as would be used in the end locking holes 19 of FIGS. 14 and 15.

Figure 22:
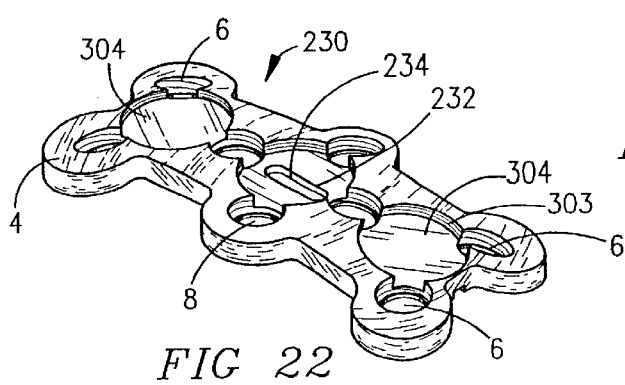
FIG. 22 is a top perspective view of a third embodiment of a cervical spine multiple locking plate utilizing locking elements in the form of threaded caps.

Referring to FIG. 22, another alternative embodiment of a multiple locking plate is shown and is generally referred to by the number 230. The plate 230 uses threaded caps, such as cap 300 shown in FIGS. 9 and 23, for a locking element or preferably one with cut outs as described having an appearance in a top view such as the locking element in FIGS. 10–11, for example. The central locking hole 232 has an elongated slot 234 for providing an increased compression capability, as will be discussed further herein.

Figure 21:
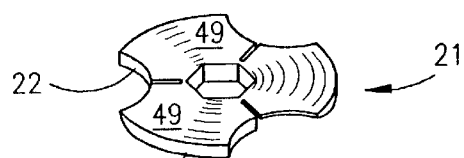
FIG. 21 is a top perspective view of the head portion of a three bone screw locking element.

Referring to FIGS. 10–13, a first embodiment of a locking element 20, 21, 25 in the form of locking screws according to the present invention for use with plate 2 is shown. FIG. 10 is a top plan view which illustrates the head 23 of the central locking element 25 shown in FIG. 7. The shaft 46 of locking element 25 is threaded 47 to mate with the threading 3 within the associated locking hole 12 of plate 2. As shown in FIG. 21, each segment 49 on each side of cutouts 22 of the locking element 21 has a bearing surface 48 formed at the lower surface of locking element head 23. As shown in FIG. 16, the locking element head 23 can be provided with two slots 42 for providing flexibility to the locking element head 23 to assist in the locking element's ability to ride over the top of the bone screw head 32 during the bearing action when the locking element is rotated. Alternatively, it is appreciated that the bearing surface can be cammed, ramped or wedged. The cammed, ramped or wedged features can also be used with the other locking elements described herein.

Referring to FIGS. 6 and 10–13, it will be appreciated that when the locking elements 20, 21 are rotated in the clockwise direction with respect to the view of FIG. 6, a respective bearing surface 48 (as best seen in FIG. 21) will ride upon the curved top surface 39 of a respective bone screw head 32 in order to positively lock the associated bone screws 30 and the locking elements 20, 21 in place.

Alternatively, as shown in FIGS. 12 and 13 in place of a bearing surface 48, a ramp or wedge shaped surface 44 may be used to increase the force applied to the bone screw head 32. When locked, the leading end of the ramped portion of the locking element would be lower than the prominence of the bone screw head 32 so that more force is needed to lift the locking element and untighten it than is needed for the locking element to remain tight and locked. However, the locking element heads 23 need not have slots, be cammed, or have a ramped surface to achieve the locking of the bone screw 30 in place. Pressure, friction, interference fits, or other engagement means capable of preventing the locking element from moving from its locked position may be employed.

Figure 20:
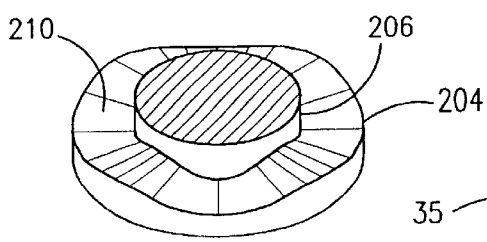
FIG. 20 is a top perspective view of the bottom portion of the head of rivet of FIG. 19 viewed along lines 20—20.

The rivet 202, shown in FIGS. 17–20 is intended for use in association with plate 70 shown in FIGS. 14–15, is shown in detail in cross section in FIGS. 19 and 20. The rivet 202 has a head 204, a shaft 206, and an elongated bottom segment 208 for fitting within the corresponding opening 200 in the plate 70. The lower surface 210 of the head 204 of the rivet 202 has an irregular surface which may be cammed, such as on the bottom of locking element 20, 21, for engaging the top surface 39 of the bone screw head 32. For use in the end locking holes 19, the upper surface of the elongated bottom segment 208 can have an irregular surface for cooperating with the irregular surface of the bottom of the plate 70 to hold the rivet 202 in the locked position against the bone screw head 32, as shown in FIG. 15. While the rivet of FIG. 18 is a separate, removable component from the plate, the rivets, and particularly those for use with the end locking holes, can be formed as part of the plate during the manufacturing process of the plate and rivet can be non-removable.

Each of the above embodiments provides tight attachment of the locking element relative the bone screw 30 and relevant plate.

Figure 23:
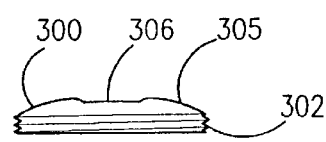
FIG. 23 is a side elevational view of a locking element for use with the plate of FIG. 22.

In the alternative embodiment of multiple locking plate 23 shown in FIG. 22, the locking element can be in the form of threaded locking cap 300 shown in FIG. 23. The threaded locking cap 300 has a thread 302 on its outer circumference corresponding to the thread 303 on the inner circumference of the locking element depressions 304 in the top of the plate 230 shown in FIG. 22. The locking cap 300 is relatively thin, particularly compared to its width. The top 305 of locking cap 300 is provided with a noncircular through hole 306 for receiving a similarly configured driving tool.

Referring to FIGS. 28, 29, and 30 another embodiment of the multiple locking plate generally referred to by the number 400 and a locking element in the form of a thin locking member 412 are shown. Plate 400 has an opening in its top surface for insertion of the thin locking member 412, a recess 402 associated with each of the bone screw receiving holes 408 and a slot 410 in the side wall of the bone screw receiving holes 408 to permit the thin locking member 412, having a series of thin projections or blades 414, thinner than the slot 410, that give this locking member 412 an appearance similar to that of a propeller. The thin locking member 412 is able to be rotated within the plate so as to not cover the bone screw holes, thus allowing the thin locking member 412 to be pre-installed prior to the installation of the bone screws by the surgeon. Limited rotation of the thin locking member 412 allows the blades 414 to protrude through the slot 410 and to cover a portion of the top of the associated bone screws 30. The blades 414 of the thin locking member 412 are flexible and, when rotated, slide over the top surface 39 of the bone screw head 32 to lock the bone screw 30 in place. As with the other embodiments discussed, each of the embodiments of the locking element is capable of locking more than one bone screw 30. It is appreciated that the various multiple locking plates and locking element combinations are capable of locking as many as four bone screws at once, but are equally effective for locking a lesser number or none at all, that is securing itself to the plate.

It will be noted that one characteristic of each of the above described locking element embodiments is to have a driver engagement means, in these cases for example, a recess 24 as large as the recess 34 in the bone screws 30 so that the same tool can be used to turn both the bone screws 30 and the locking elements. Also, the locking elements are sufficiently strong and have sufficient mass so as to be able to withstand being locked without breakage.

Figure 40:
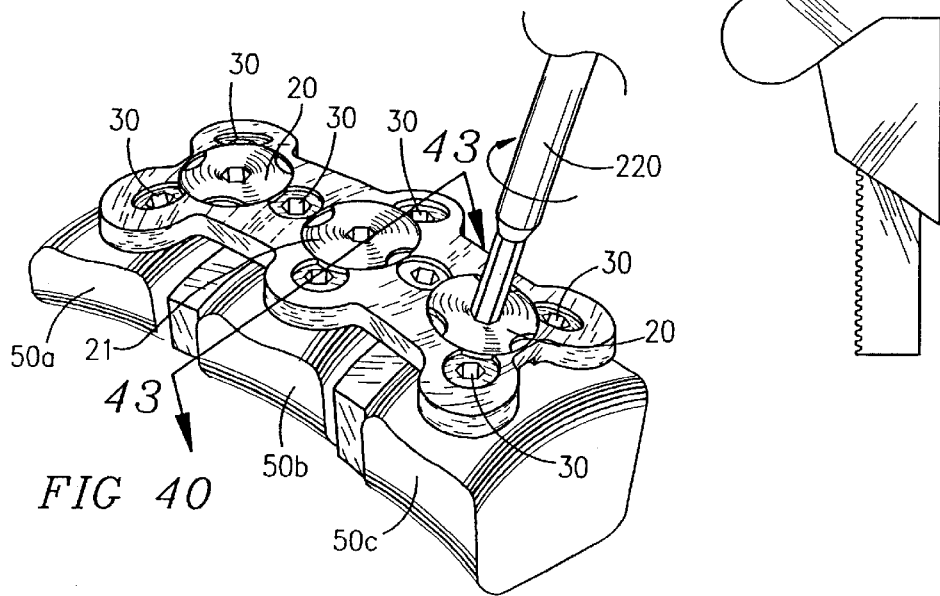
FIG. 40 is a top perspective view showing the locking of the bone screws to the plate.
Figure 41:
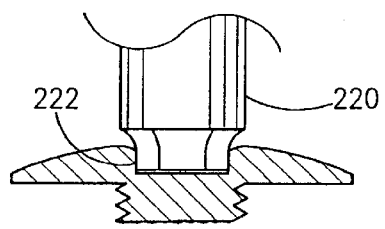
FIG. 41 is a partial side sectional view of a locking element attached to a driver instrument.
Figure 42:
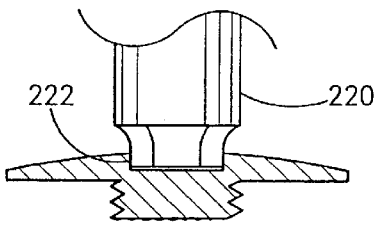
FIG. 42 is a partial side sectional view of another embodiment of the locking element attached to a driver instrument.

All of the shown examples.of the multiple locking elements that have a number of cutout portions have an arc with a radius greater than that of the bone screw head. In addition, the head 23 of each locking element 20, 21 is provided at its center with a noncircular recess 24, such as shown in FIG. 9 which is engageable by an appropriate manipulation tool, such as shown in FIGS. 40–42. In the embodiment of head 23 shown in FIG. 9, the associated tool would have a hex head, but as discussed with regard to FIGS. 80 and 81, other shapes of recesses in the head 23 may be used. The thread of each locking hole 12 and of each locking element 20, 21 has a close tolerance so that they will reliably retain their orientations so as to permit introduction of bones crews 30 into bone screw receiving holes 6, 8 without interference.

Figure 83:
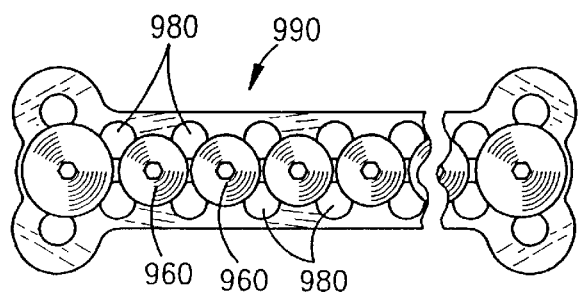
FIG. 83 is a further embodiment of a cervical spine multiple locking plate for use in stabilizing multiple segments of the spine.
Figure 84A:
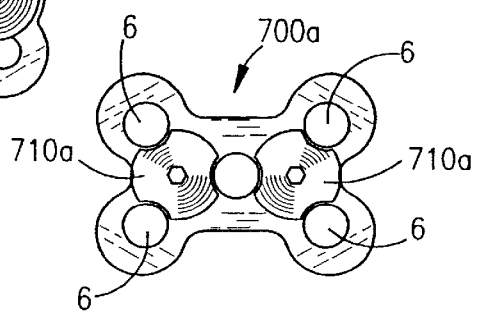
FIGS. 84A–84E are various embodiments of cervical spine multiple locking plates for use in stabilizing a single segment of the spine.
Figure 84B:
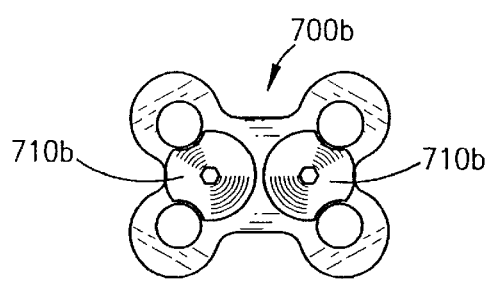
Figure 84C:
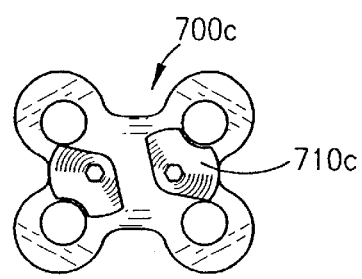
Figure 84D:
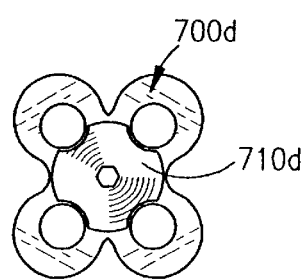
Figure 84E:
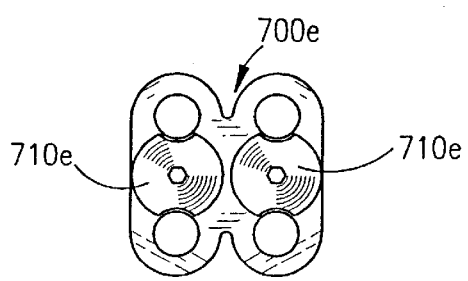

It is appreciated that while various forms of locking elements have been disclosed, in light of the teaching, other equivalent means can be used for the purpose of locking the bone screws 30 in place. In FIG. 83, an alternative multiple locking plate 990 is shown having additional intermediate bone screw receiving holes 980 and associated locking elements 960 for locking bone screws 30 in place. Plate 990 allows for a more close spacing and more pairs of bone screw holes than the number of vertebrae to be engaged.

In FIGS. 84A–84E various plates 700*a–g* used for a single level fusion are shown. Each of these plates 700*a–g* is designed to span one spinal segment consisting of one disc space and two adjacent vertebrae (containing the bone graft), and have bone screws inserted into the end of the vertebrae through the bone screw receiving holes 6 associated with the two adjacent vertebrae and then locked in place. As shown in FIGS. 84A–84E, one locking element 710, or two locking elements can be used to lock four bone screws in place. In FIGS. 84A–84E, each of the plates 700*a–e* is shown with the locking-elements in their open orientation, before being rotated to lock the bone screws.

Each of the above described plates can have the same generally biconcave contour as already described for conforming to the anterior aspect of the spine.

Figures 24A, 25:
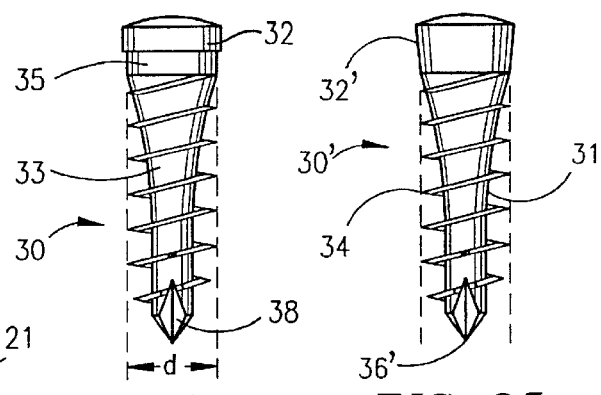
FIG. 24A is a side elevational view of a bone screw in accordance with the resent invention.
FIG. 25 is a side elevational view of an alternative embodiment of a bone screw in accordance with the present invention.
Figure 27:
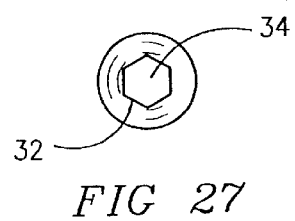
FIG. 27 is a top end view of the bone screw shown in FIG. 24A.

FIGS. 24A and 24B provide a side view of one embodiment of a bone screw 30according to the present invention. FIG. 27 is a top view of the bone screw 30. At the center of bone screw head 32 is a profiled recess 34 which may have the same form as the recess 24 of each locking element 20, 21 in which case it may be turned with the same tool as that employed for turning locking elements 20, 21. It is appreciated that the driver engaging portion of the bone screw 30 could be slotted, and be either male or female (as is shown).

In the embodiment of bone screw 30 shown in FIGS. 24A and 24B, the bone screw head 32 is stepped, with the first lower head portion 35 being contiguous with the screw shank 33 and has a smaller diameter than the upper portion of the bone screw head 32. When this embodiment of bone screw 30 is employed, each bone screw receiving hole 6, 8 of the plate 2 has a countersunk region 14 matching the diameter of the upper portion of the bone screw head 32 and dimensioned for an interference fit. The lower portion 35 of the bone screw head, 32 is dimensioned to achieve an interference fit with its associated portion of bone screw receiving holes 6, 8. The larger diameter upper portion of bone screw head 32 assures that the bone screw 30 cannot be advanced completely through bone screw receiving holes 6, 8 of plate 2. The bone screw 30 passes completely through the upper surface of the plate 2 without engaging the upper surface in any way.

Figure 44:
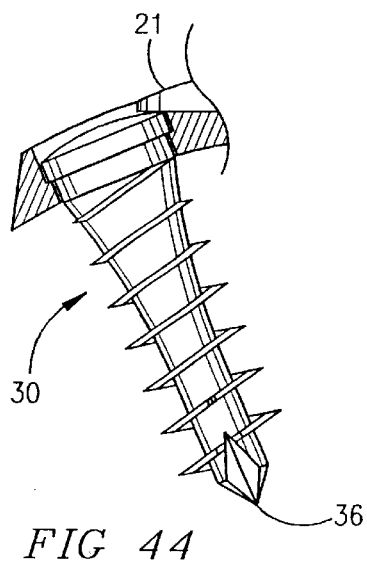
FIG. 44 is an enlarged portion of detail along line 44 of FIG. 43.

As shown in FIG. 44, the head 32 of screw 30 passes unobstructed through the upper surface of the plate until the lower surface of enlarged screw head 32 engages the upper face of the narrowed bone screw receiving portion at the midsubstance or below the midsubstance of the plate. This is considered optimal for allowing for the greatest screw to plate stability, even absent the lock, against all forces except those reverse the path of insertion, while still providing for the greatest plate strength beneath the bone screw head 23. That is, since the plate is of only generally 2–3 mm in thickness, a sheer vertical circumferential wall is best able to constrain the motion of a screw if the head is similarly configured and there is little tolerance between them. Placing the support of the head near the mid thickness of the plate is preferred as it allows the head to remain large to accommodate the recess for the driver without being weakened, while placing the support of the head away from the upper surface of the plate allows the screw head to be deep into the plate. Placing the support of the head at approximately the mid thickness of the plate assures plenty of plate material beneath the head to support while providing adequate head length above and below the contact point to prevent the contact point from acting as a fulcrum by providing adequate lever arms to prevent unwanted motion.

In the alternative embodiment of bone screw 30', as shown in FIG. 25, bone screw head 32' is tapered in the direction from the top of the bone screw head 32' toward screw tip 36'. Again, the bone screw head 32' is dimensioned to achieve an interference fit in the associated bone screw receiving hole 6, 8 when the bone screw 30' has been fully installed. When this embodiment of bone screw 30' is employed, bone screw receiving holes 6, 8 need not be provided with a countersunk region 4.

In each of the above embodiments of the bone screws, the bone screws 30 and 30' present a unique combination of a tapered screw shaft 33' and a helical thread 31. The diameter of screw shaft 33 generally increases.-from a distal portion of the shaft near the screw tip 36 toward the proximal portion of the shaft near screw head 32. In the preferred embodiment, the rate of increase in diameter is also greater near the bone screw head 32. Such a shape avoids stress risers and provides increased strength at the screw-plate junction, where it is needed the most. The tapering of screw shaft 33 may have a concave form, as shown in FIG. 24A, or may be linear. The distal portion of the screw shaft 33 may assume a constant diameter.

Referring again to FIGS. 24A and 24B, the thread 31 of the bone screw 30 has a substantially constant outer, or crest, diameter "d" from the proximal portion of the shaft below the bone screw head 32 to the distal portion of the shaft near the bone screw tip 36. In the screw tip 36, the crest diameter of thread 31 may be reduced for preferably one to two turns to facilitate the insertion and penetration of the bone screw 30 into the bone.

In the preferred embodiment, the thread 31 of each bone screw 30 has an outer diameter slightly smaller than the diameter of the lowest portion 35 of the bone screw head 32, which is adjacent the trailing, or upper, end of the associated thread 31. In addition, the thread 31 is relatively thin, in the direction of the longitudinal axis of the screw, and tapers outwardly, and has a cross section of a triangle.

An example of the dimensions of a bone screw for use in human anterior cervical spinal surgery for insertion into the vertebrae is as follows: the threaded portion of said screw has a length from about 10 mm to about 22 mm (12–18 mm preferred) and a head length from about 1 mm to about 3 mm (2–2.5 mm preferred). The threaded portion should have a maximum outside diameter from about 3.6 mm to about 5.2. mm (3.8–4.5 mm preferred) and the head has a diameter from about 3.8 mm to about 6 mm (4–5.5 mm preferred). The thread pitch is from about 1.25 mm to about 2.5 mm (1.5–2.0 mm preferred) and has a sharp and thin threaded profile. The apex of the two faces of the thread have an angle of less than about 21 degrees (15 degrees, preferred) and the base of the thread is less than about 0.60 mm thick (0.25 mm–0.35 mm preferred). The screw has a root diameter that increases from proximately above the tip of the shank, along the longitudinal axis to proximately below the head portion of the screw. Preferably, the tip of the screw tip is fluted by at least one cut out section so as to make the screw self-tapping.

Even though the thread 31 of the bone screw 30 has a thin profile, the thread will nevertheless be stronger than the bone into which it is introduced so that this thread will efficiently cut a thin helical groove in the bone tissue. The volume of bone that will be displaced by the thickness of the thread is minimized by the, thin form of the thread, yet the substantial crest diameter of the screw thread maximizes the surface area of the threads in contact with the bone. While enlarging the screw shaft 33 diameter near the bone screw head 32 increases its strength where needed, reducing the screw shaft 33 diameter away from the bone screw head 32 where such strength is not required allows for the maximum area of engagement, for the thread 31 to the bone.

Figure 26:
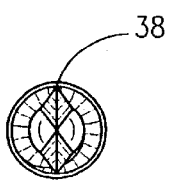
FIG. 26 is a bottom end view of the bone screw shown in FIG. 24A.

In the preferred embodiment, as shown in FIGS. 24A and 26, bone screw tip 36 is provided with cutting flutes 38, to make the bone screw 30 self-tapping. Unlike the prior art bone screws, used for anterior cervical spinal surgery which are not self-tapping, the thread form of the present invention screw is itself more like a tap than a conventional screw in that the threads are very sharp and fluted. Additional embodiments of the bone screws 30 is shown in FIGS. 53–55.

By way of example, plates for fusing three adjacent vertebrae (2 interspaces, or two spinal segments) are shown. Each set of the bone screw receiving holes associated with a vertebrae is considered to be a segment of the plate so that for example, in FIG. 1 three segments are shown—an upper, a central, and a lower segment. While the present discussion is in association with plates for use in fusing three vertebrae across two interspaces, it should be understood that longer and shorter plates having the appropriate number and location of bone screw receiving holes corresponding to the number of vertebrae to be fused are contemplated, and would take the form of the plates shown with fewer or more intermediate segments, such as the segment along line 9 of FIG. 1, or the intermediate segments of the plates shown in FIGS. 82–84F.

Referring to FIGS. 31–42, an outline of the steps of the method for installing the plates of the present invention is set forth below. A detailed description of the instrumentation and method for installing the plates of the present invention follows the outline.

Step 1

Having completed the interbody fusions, the surgeon removes any bone spurs or localized irregularities along the front of the spine of the area to be fused.

Step 2

The correct length plate is selected by the surgeon by measuring the distance on the spine by a caliper, ruler, template, and the like. That plate having a length sufficient to span the distance of the spine to be fused and to partially overlap a portion of each of the end vertebrae to be fused.

Step 3.

Utilizing a plate holder, the plate is placed into the wound and positioned to confirm positioning, length, and screw hole alignment relative to the segments of the spine to be fused.

Step 4.

Figure 31:
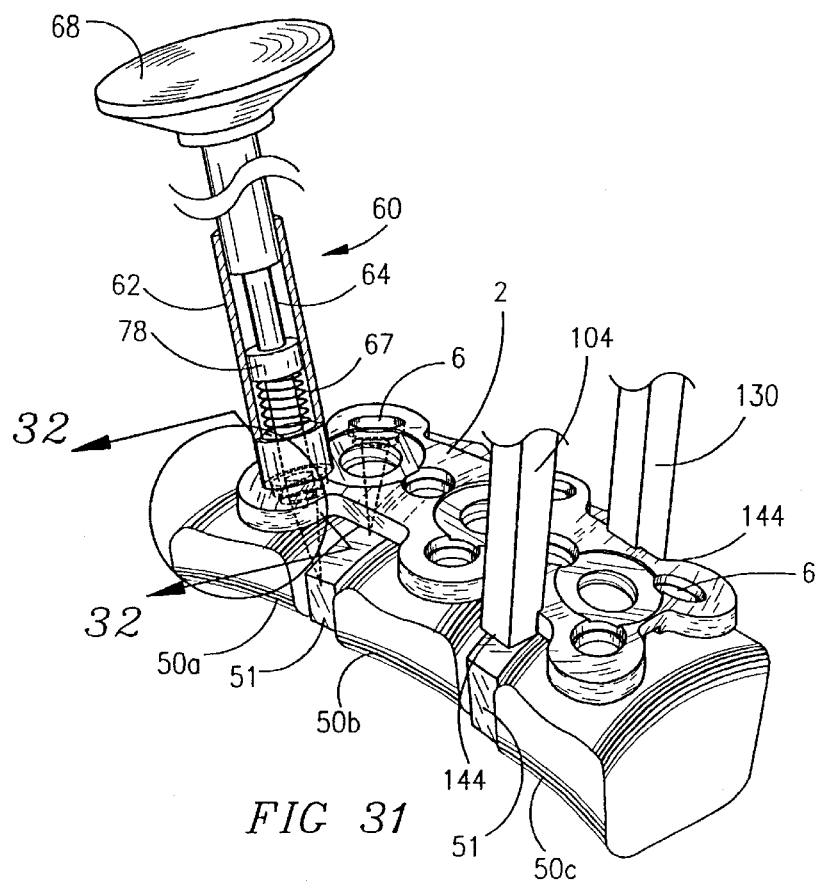
FIG. 31 is a top perspective view of the plate of FIG. 1 positioned against the anterior aspect of three successive vertebral bodies in the cervical spine a plate holder, and an instrument for forming bone screw receiving holes in to the vertebral bodies.

As shown in FIG. 31, with the plate thus positioned and securely held, the plate may be attached to any of the vertebrae to be fused (by example only, here shown as the top vertebra).

Sub-Step 4A

Figure 32:
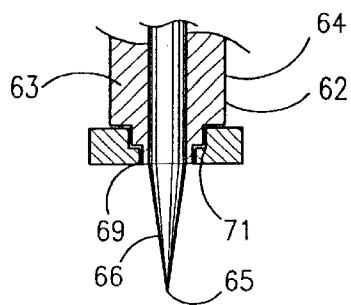
FIG. 32 is a cross-sectional view of a portion of the bone forming device shown in FIG. 31 viewed along lines 32—32.
Figure 37:
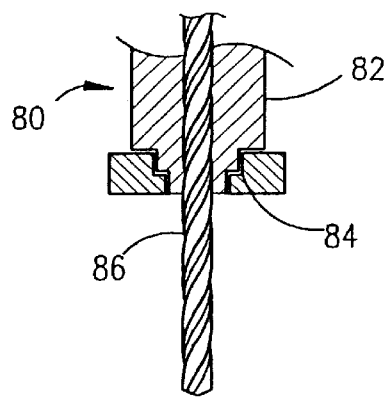
FIG. 37 is a.cross-sectional view through the plate of an alternative embodiment of a hole forming instrument in the form of a drill guide and drill for use during the plate installation procedure.

The pilot (guide) hole punch 60 is attached to the a plate 2 as,per FIG. 32, or alternatively, while not preferred the drill guide may be used as per FIG. 37. In either event, the pilot hole forming means rigidly aligns with and is captured by the plate bone screw receiving hole wall.

Sub-Step 4B

The pilot hole is then formed by impacting the pilot hole punch of FIG. 32 or drilling with the drill of FIG. 37. In the alternative while not preferred, the formation of the pilot hole can Me done away with altogether and the correct screw selected so as to have a length less than the distance along its path to the posterior vertebral cortex can be directly inserted.

The determination of the appropriate screw length is made by measuring or templating from radiographs, MRI's, or CT scans, or determined directly by measuring the depth of the disc space.

Step 5

Figure 80:
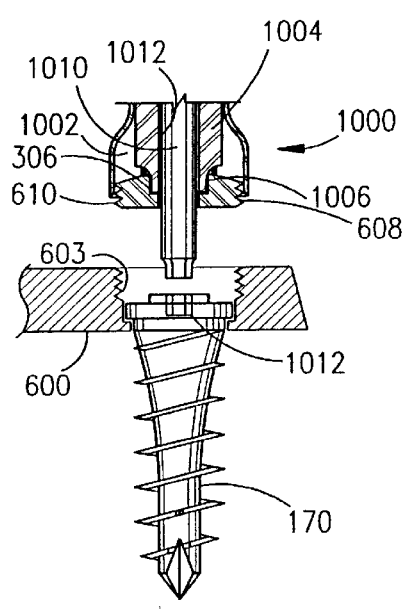
FIG. 80 is a partial cross sectional view of a plate and bone screw with the end of a tool shown for use in inserting both the bone screws and locking caps.

The correct screw is then attached to the screw driver which regardless of the specific form of the screw driver engagement means, is designed to have an interference fit so as to remain firmly bound to the driver during transport to the insertion site. FIGS. 41, 42, 63, 64, 80 and 81 show various ways of achieving such a fit of the driver and screw. In addition to a wedging at the screw and driver interface, clips, and springs and other means are well known for temporarily and reversibly securing the screw to the driver, such as is shown in FIG. 80 where a slotted inwardly springing sleeve holds a threaded cap peripherally until, as it is screwed into the plate, it is automatically pushed back releasing the threaded cap.

Figure 33:
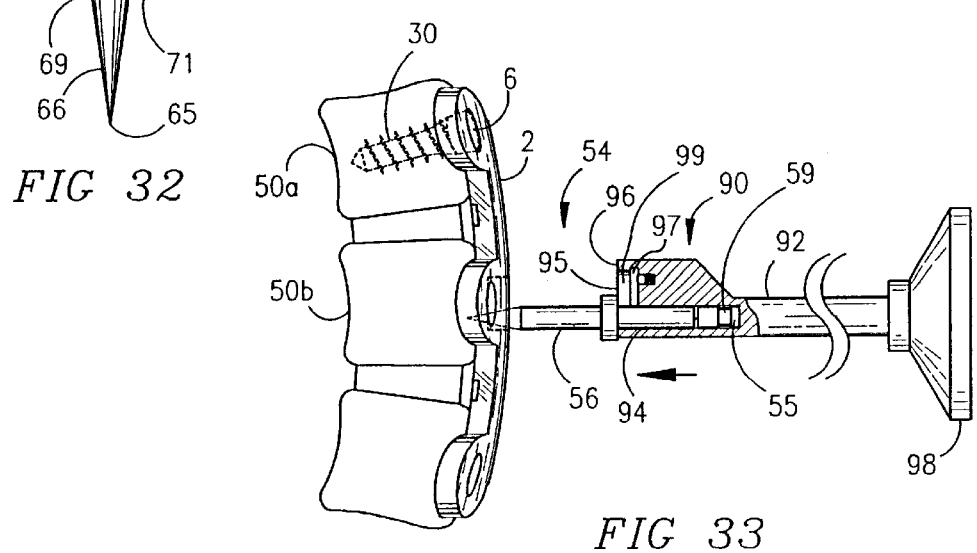
FIG. 33 is a side elevational view in partial cross section illustrating a compression post tool and a compression post engaged to it for insertion into a vertebral body.

Once a first bone screw has been fully inserted into a vertebra through the plate, it is preferable to insert the other of the transverse pair in the manner already described as per FIG. 33.

In a similar manner, it is possible to insert the remaining bone screws as per the surgeon's preference into each of the vertebrae to be included into the fusion, just the end vertebrae of the fusion construct, or additionally place screws into the fusion grafts.

However, as shown in FIGS. 33, 34, 38 and 39, it is possible with the present invention at the surgeon's option to place any portion or all of the fusion construct under compression and to do so intersegmentally or across the entire length of the fusion construct even when multisegmented.

It is appreciated that the same procedure could be generally.used for any of the plate systems of the present invention.

As shown in FIG. 31, the vertebrae 50a–c are separated from one another by fusion graft blocks 51 which were previously installed in the spinal disc space between adjacent vertebrae 50 forming a fusion bone graft construct. Plate 2 is shown in FIG. 31 with the locking elements 20, 21 removed in order to simplify the illustration. It will be understood, however, that in the preferred embodiment the locking elements 20, 21 can be, and preferably are, preinstalled in the positions shown in FIG. 6 prior to positioning plate 2 upon vertebral bodies of the vertebrae 50, thereby saving the surgeon time and trouble.

Figure 39:
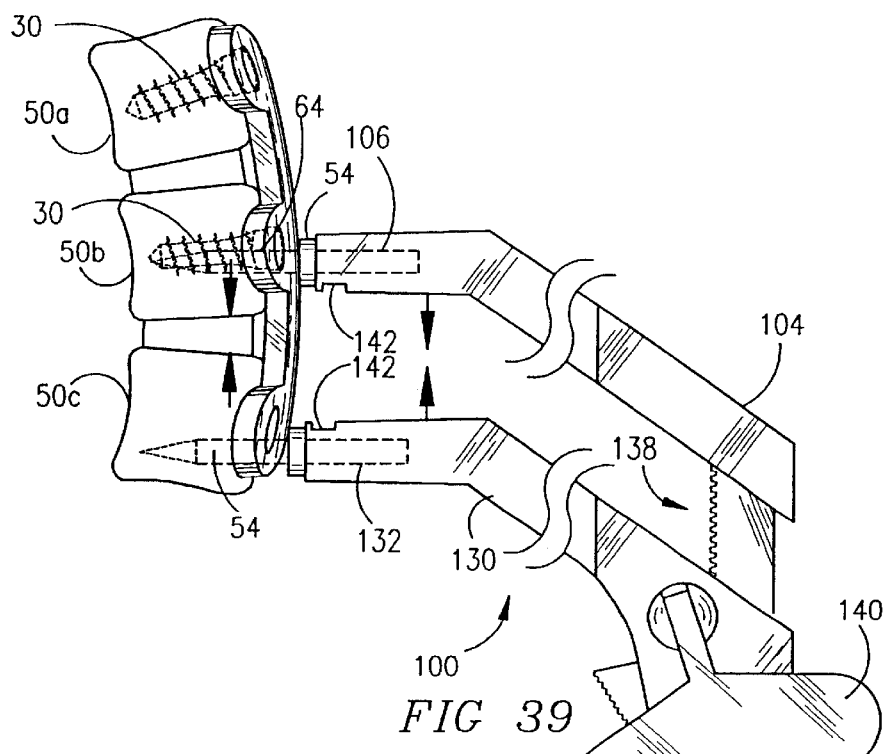
FIG. 39 is a view similar to that of FIG. 38 showing the compression apparatus in a further stage of the plate installation procedure.
Figure 45:
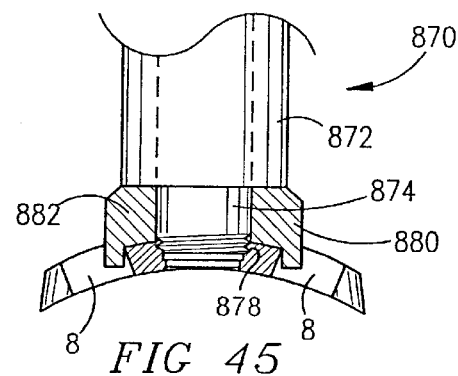
FIG. 45 is a side view in partial cross section of a plate holder attached to a plate.
Figure 46:
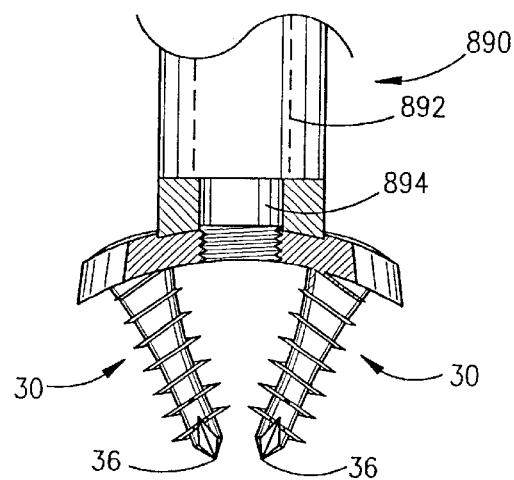
FIG. 46 is a side view in partial cross section of another embodiment of a plate holder attached to a plate.
Figure 61:
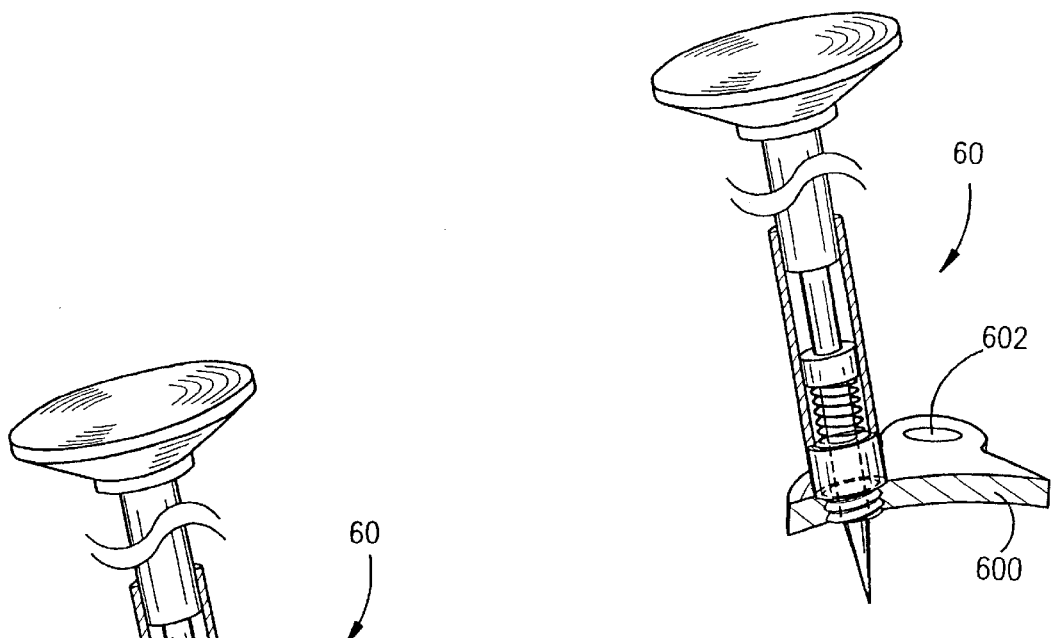
FIG. 61 is a side elevational view in partial cutaway of the hole forming instrument threaded to a bone screw receiving hole.
Figure 60:
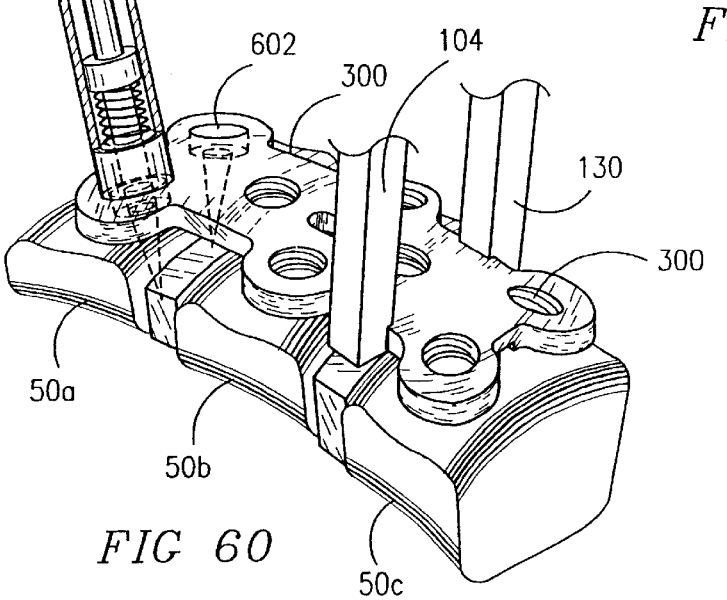
FIG. 60 is a top perspective view of the single locking plate of FIG. 47 shown being held by a plate holder against three vertebral bodies, with the hole forming instrument for punching a pilot hole into the vertebral bodies for receiving a bone screw.
Figure 62:
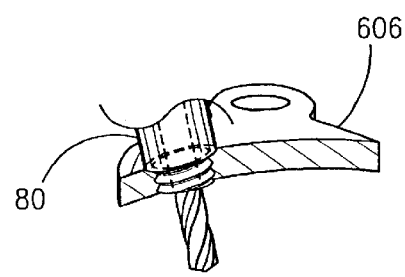
FIG. 62 is a perspective side sectional view of the drill and drill guide threadably engaged to the plate for drilling a hole for insertion of a bone screw.
Figure 70:
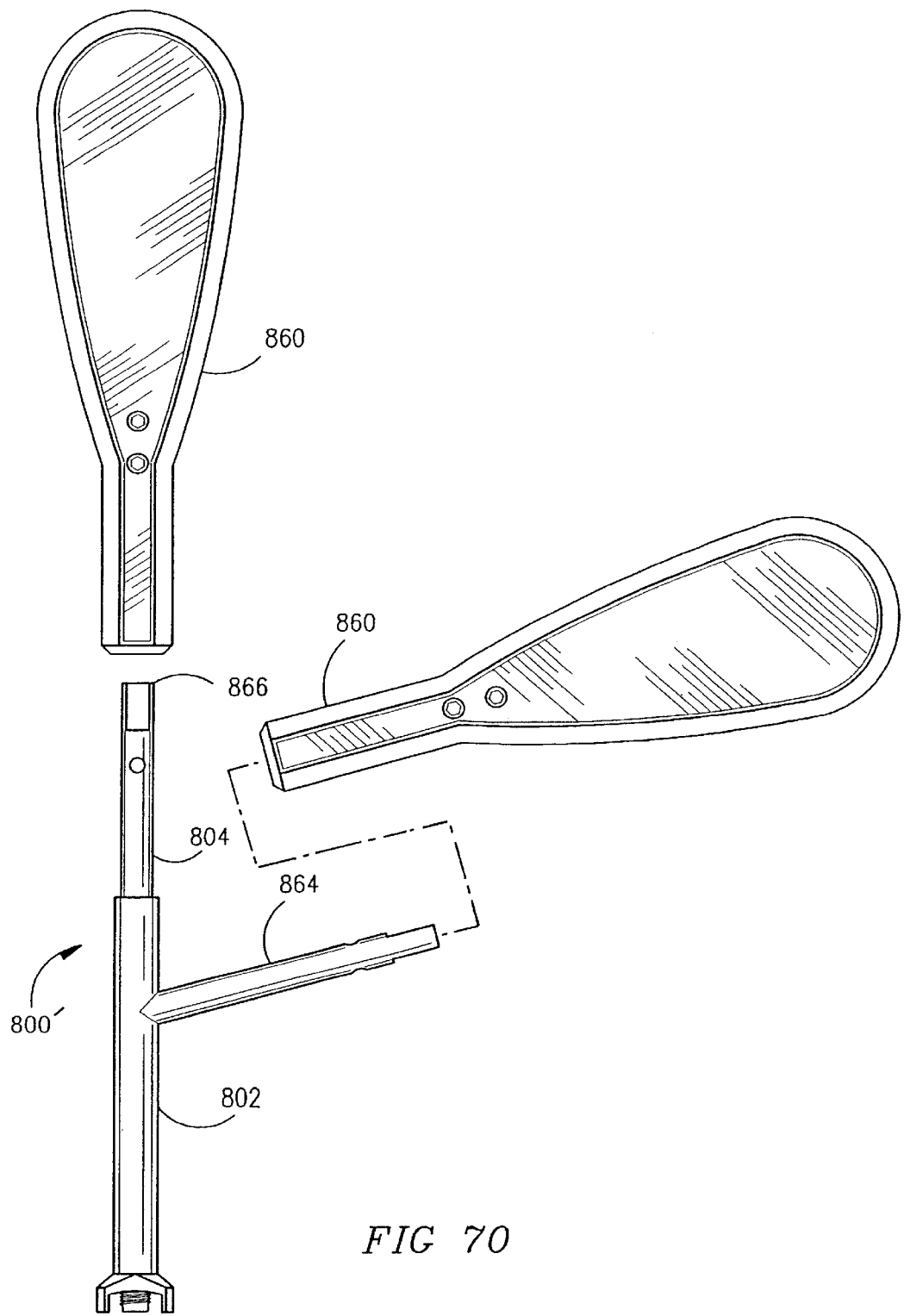
FIG. 70 is a plate holder instrument with an offset and removable handle.

Plate 2 may be held in position by any known plate holding means, but preferably by the holding tools shown in FIGS. 45, 46 or 70 by the notches 142 in the sides of the compression arms 104, 130 of a vertebral compressor tool 100 shown in FIG. 39, or as a further alternative, by the unitary plate holder similar to the FIG. 70 design.

As shown in FIG. 45, plate holder 870 has a hollow tubular housing 872, with a central rod 874 having a thread 878 at one end for engaging one of the threaded locking holes 12 in the plate 2. The bottom end of the housing 872 has projections 880, 882 that extend outwardly and then downwardly to fit into the bone screw receiving holes 8 of the plate 2 preventing the housing 872 from rotating. The central rod 874 is located in the housing 872 such that it can be rotated by rotating a handle (not shown) which is fixed to the central rod 874 at its upper end.

In FIG. 46 an alternative embodiment of the plate holder 890 is shown. A single solid member 890 has a threaded projection 894 at its bottom end for attachment to the central threaded locking hole 12 in the plate. The bottom surface of the holder 890 of this embodiment is contoured so as to match the contours of the top surface of the plate adjacent to the locking hole 12, shown as a depression 14 (FIG. 1).

Referring to FIGS. 67–68, an embodiment of a plate holder for holding any of the plates while being positioned on the vertebrae is shown and generally referred to by the number 800. The plate holder 800 has a hollow tubular housing 802, with a central rod 804 having a handle 806 at one end and a thread 808 at its other end for engaging one of the threaded locking holes 12 in the plate 600. The bottom end of the housing 802 has projections 810, 812 that extend.outwardly and then downwardly 814, 816 to fit along the side edge of the plate 2 between the end and intermediate lobes 4, preventing the housing 802 from rotating. The central rod 804 is located in the housing 802 such that it can be rotated by rotating the handle 806 which is fixed to the, central rod 804 at its upper end. This central rod 804 can also be attached to the housing 802 so that it can move up and down to some extent, by any number of conventional ways, such as by having the central rod 804 have an annular depression with a length of approximately 3–5 mm, and.a set screw projecting inward from the housing to engage the central rod 804. Once the plate 600 is in the proper place and the plate is attached to one of the vertebrae by bone screws 30, the central rod 804 is disconnected from the opening in the plate 600 and the holder 800 is removed.

FIG. 69A is an alternative embodiment of the plate holder 850. A single solid member 852 has a threaded projection 854 at its bottom end for attachment to the central threaded locking hole 12 in the plate. The solid member 852 could also be threaded into a bone screw receiving hole 6. The bottom surface of the holder 850 of this embodiment is contoured so as to match the contours of the top surface of the plate adjacent to the locking hole 12, shown as a depression 14 (FIG. 1).

FIG. 69B is another embodiment of the plate holder 850'. A housing 851' having an end 853' configured to engage a bone screw receiving hole 6 contains a rod 855' having an uneven diameter and having a threaded portion 857'. As rod 855' is rotated by a handle similar to handle 806 shown in FIG. 68, rod 855' screws downward into the housing 851' into matching threads 858'. As the end of rod 855' is driven down, it spreads portions 859a' and 859b' (859c' and 859d' not shown) wedging plate holder 850' into a bone screw receiving hole of the plate. Plate holder A 850' is best used with non-threaded bone screw receiving holes, but works for all types of bone screw receiving holes.

Referring to FIG. 70, an alternative embodiment of the plate holder referred to by the number 800" is shown in which there is a removable handle 860 that is used for first attaching the plate holder 800" to the plate, by rotating the shaft 804, and then for holding the plate holder 800" off to the side by extension 864, during the attachment procedure reducing the interference of the plate holder 800" with the surgical procedure.

Figure 38:
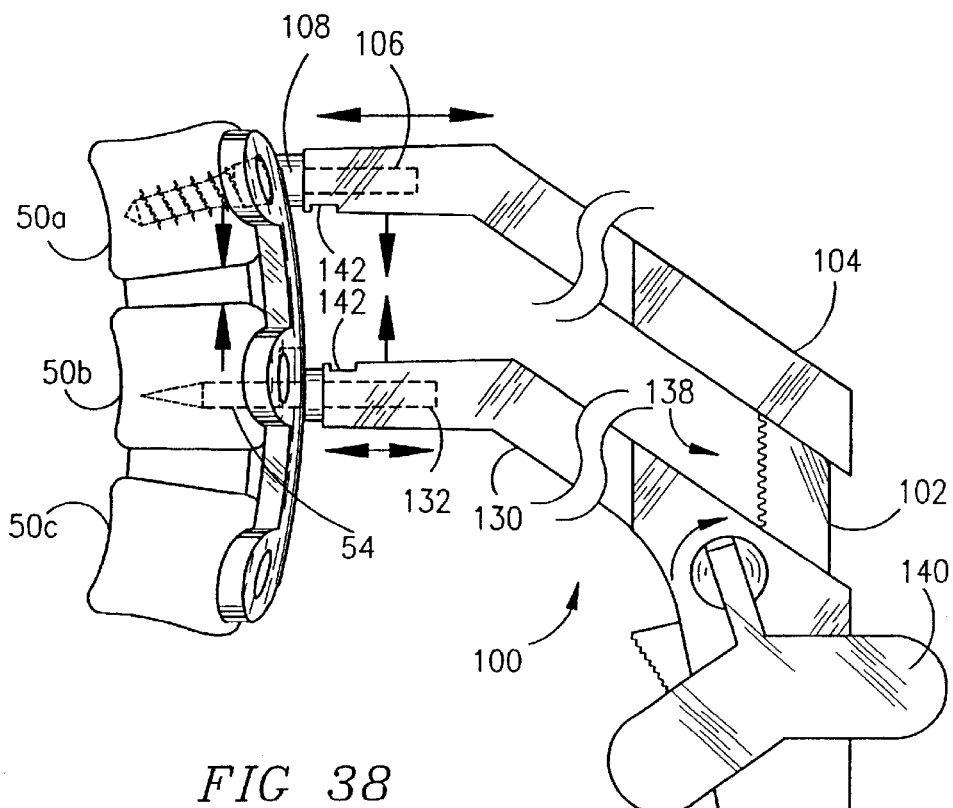
FIG. 38 is a side elevational view showing intersegmental compression of the spine and compression apparatus.

Referring to FIG. 38, a compression tool 100 is shown with a toothed gear bar 102 having a first compression arm 104 secured to its free end. Compression arm 104 has at its distal end a bore 106 for removably holding either a plate engaging element 168, shown in FIG. 36, having a hook 110 at one end for engaging a depression or notch 18 in the end of plate 2, or for removably holding a compression post 54 shown in FIGS. 33–34. As shown in FIG. 36, plate engaging element 108 includes a shaft 112 that will be inserted into the corresponding bore 106 of compression arm 104, and a flange 115 for resting against the bottom face of bore 106 to accurately limit the depth of insertion of plate engaging element 108 into the bore 106. A ring spring 128, preferably of metal, is located in an annular depression of the shaft 112, for holding the plate engaging element 108 in the bore 106.

Referring to FIGS. 38–39, compression tool 100 includes a second moveable compression arm 130 movable along toothed bar 102 parallel to first compression arm 104. The distal end of the second compression arm 130 also has a bore 132, the same as bore 106, that ran receive a removable compression post 54. Bores 106 and 132 are the same so that either compression arm 104, 130 can be used to hold the removable compression post 54, permitting the compression tool 100 to be used in any orientation. By permitting the plate engaging element 108 and the compression post 54 to both rotate and slide in the bores 106, 132 of the two compression arms 104, 130, with the plate engaging hook 110 able to work even at an angle to the plate allows for the apparatus to be readily attachable to the spine through the compression post 54 and plate.

Compression arm 130 has a driving assembly consisting of a toothed wheel (not visible) which is engaged with the tooth gear 138 of bar toothed gear 102 and is connected to compression arm 130 such that compression arm 130 is movable along the length of toothed gear bar 102 by means of the rotation of handle 140, which is connected to the toothed wheel. When the handle 140 is turned in the direction of the arrow shown in FIG. 38, compression arm 130 is moved toward compression arm 104. The driving assembly has a self lock release mechanism whereby the movement of the two compression arms 104, 130 away from one another is prevented, without the activation of the release. On the inward distal end of each compression arm, on facing sides, is a notch 142 or recess for holding the plate 2 along its sides between the central lobes 4 and end lobes 4, as shown in FIG. 38.

While the toothed gear bar 102 and compression arms 104, 130 have been described as being straight, it is possible that the toothed gear bar 102 and compression arms 104, 130 may be arcuately or otherwise shaped, so as to induce lordosis in the vertebrae, if so desired.

As shown in FIG. 31, in the event that the compression tool 100 is used to hold the plate 2, the ends 144 of the compression arms 104, 130 will.be located in line with the fusion graft construct 51 which was placed in the disc space when plate 2 is properly positioned. A gap will exist between plate 2 and each fusion graft construct 51, providing a space to accommodate the free ends of arms 104, 130 should they extend beyond the bottom surface of the plate 2. As will be described below, the same compression tool 100 can also be used for compressing a plurality of cervical vertebral bodies with bone grafts interposed during the attachment of plate 2 to the vertebrae 50.

Referring to FIG. 31, plate 2 is held by a suitable holder, in this case shown as the compression arms 104 and 130. Once the appropriate length plate 2 has been properly positioned so that the bone screw receiving holes 6 are aligned with each of the respective vertebrae 50a–c to be fused, the next step is the formation of bone screw receiving holes 6 prior to installation of the bone screws 30 themselves in the vertebrae 50a. While the procedure is described as first attaching the plate 2 to the upper vertebrae 50a, the plate 2 can be attached to any of the vertebrae in any order. Different sized plates are used so that, as indicated above, the physician will select the appropriate sized plate in which the bone screw receiving holes 6, 8 are aligned with the three adjacent vertebrae 50a, 50b and 50c. Pilot holes are formed by a pilot hole forming apparatus 60 shown in FIGS. 31 and 32. Unlike with known prior art and screw plating systems, the bone screws 30 may be inserted without the prior formation of an opening into the vertebrae as the bone screws, 30 are preferably sharp pointed, self-tapping, and have at their tip a diminishing major diameter to assist the screw entering and pulling into the bone. However, while a hole into the bone of the vertebrae may be formed prior to screw insertion, it is preferable that the hole be of a smaller diameter than the root diameter of the screw and for a different purpose than with the prior art. With the prior art the hole drilled had to be of a diameter equal to but preferably larger than the root (minor) diameter of the screw, as the screws were not self-tapping. It is desirous to create pilot holes to assure that a proper path for the bone screws 30 is maintained, and also to prevent damage to the vertebral bone during insertion of the bone screws 30. In addition, the pilot hole forming apparatus 60 creates a more compact vertebral bone mass for reception of the self-tapping bone screw 30 used in this insertion.

As shown in FIGS. 31 and 32, pilot hole forming apparatus 60 includes a hollow cylindrical housing 62 having a bottom provided with a through hole 63. Housing 62 contains a central shaft 64 which extends through the through hole 63 in the bottom of housing 62. The leading end 66 of shaft 64 tapers gradually to a sharp point 65. Shaft 64 is provided with a ring member 78 having a diameter which closely corresponds to the inner diameter of housing 62 to guide the travel of shaft 64 within housing 62. A compression spring 67 is interposed between the ring member 78 and the bottom of housing 62. Compression spring 67 provides a bias force which normally urges the sharp point 65 into a retracted position within housing 62. The upper end of shaft 64 has an enlarged head 68 extending outside of the housing 62 which is intended to be manually depressed or struck by a percussion instrument in order to drive the sharp point 65 out of housing 62 and into a vertebral body 50a. Shaft 64 is given a length, taking into account the length that spring 67 will have when fully compressed, to determine the maximum depth of the pilot hole formed in a vertebral body The depth is selected to assure that the pilot hole does not reach the posterior cortex of the vertebral body, which borders the spinal canal.

Certain structural features of hole forming apparatus 60 are shown in greater detail in FIG. 32. In particular, it can be seen that the bottom end of housing 62 has a projecting portion 69 dimensioned to fit precisely in a bone screw receiving hole 6 or 8 of plate 2. The bottom 71 of the projecting portion 69 is flat in a plane perpendicular to the axis of housing 62. When the projecting portion 69 of housing 62 is snugly inserted into a bone screw receiving hole 6, 8 and the flat bottom 71 is placed flush against the upper surface of plate 2, it is assured that the leading end 66 of shaft 64 will form a pilot hole in the vertebral bone having an axis perpendicular to the plane of the associated portion of plate 2, thereby assuring that the bone screw 30 will be subsequently installed so that its axis is also perpendicular to the plane which is parallel to the upper and lower surfaces of the associated portion of plate 2.

When a plate is used which has a threaded bone screw receiving hole, the lower end of the pilot hole forming apparatus 60 is threaded so as to engage the thread in the bone screw receiving hole 6, 8 thereby fixing the plate and the pilot hole forming apparatus together, assuring a stable fit between the pilot hole forming apparatus and the plate 2. It should be noted that the diameter of the leading end 66 of the shaft 64 is small since it has to fit within the small space left between the inside wall of the pilot hole forming apparatus. Since it is only a pilot hole for a self-tapping bone screw 30 that is being formed, the small diameter is satisfactory.

Referring to FIG. 37, if for any reason it should be desired to form the pilot hole in the vertebral body 50 by drilling, rather than by the use of the pilot hole forming apparatus 60, use can be made of a drill guide 80, having a lower end as shown in FIG. 37. The drill 80 guide consists of a tubular member 82 and a small diameter lower end 84 which is dimensioned to achieve a precise interference fit in the associated bone screw receiving hole 6, 8 of plate 2. Along the small diameter lower end 84, drill guide 80 has an axial end surface in a plane perpendicular to the longitudinal axis of the drill guide 80 so that when the small diameter portion 84 is fitted into the bone screw receiving hole 6 and the surface surrounding the small diameter portion 84 is flush against the upper surface of plate 2, the axis of the drill guiding bore 86 in drill guide 80 will be precisely perpendicular to the upper and lower surfaces of the associated portion of plate 2. As with the case described above, the bottom end of the drill guide 80 can be threaded so as to engage to the threaded opening of plate 2.

After the bone screw receiving holes 6, 8 are formed in the vertebral body 50a through the upper two bone screw securing holes 6 of plate 2 by means of either hole forming apparatus 60 or drill guide 80, bone screws 30 are threaded into the vertebrae 50 while holding the plate 2 firmly against the vertebrae 50 with compression tool 100 or plate holder 800. This locks the plate to the vertebrae 50a.

Figure 34:
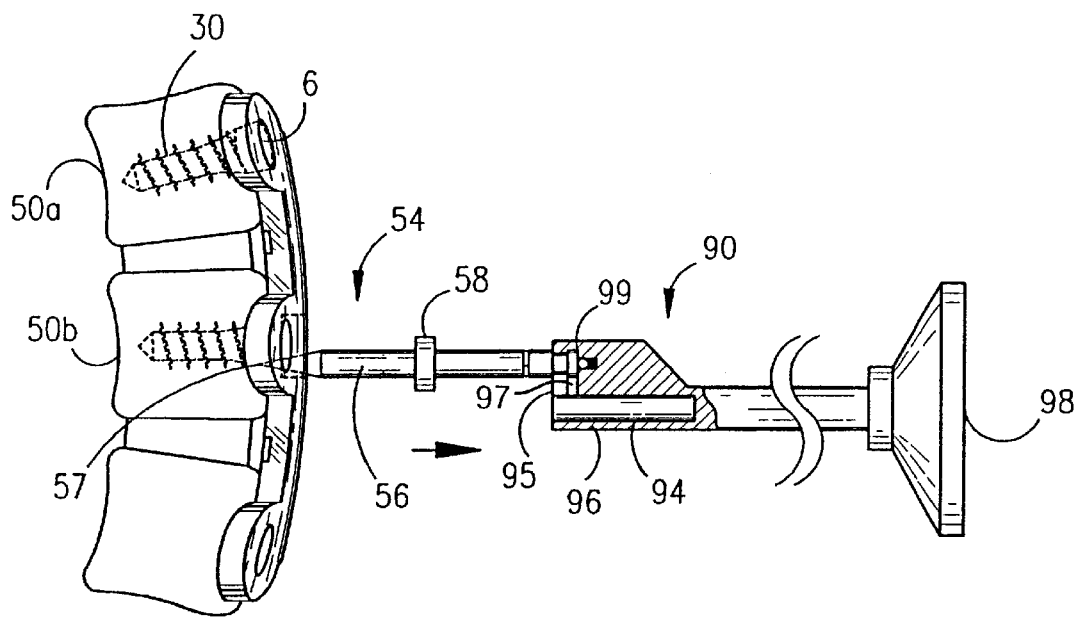
FIG. 34 is a side elevational view in partial cross section of the compression post tool engaged, for removal of the compression post from the vertebral body.
Figure 35:
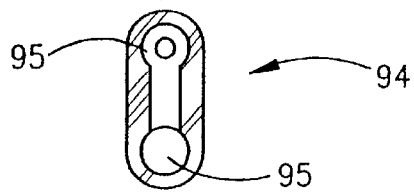
FIG. 35 is a bottom end view of the compression post tool of FIG. 34.

It is then possible, if desired, to compress the fusion graft in the next adjacent vertebrae 50b before attaching bone screws 30 to the adjacent vertebrae 50b through the central bone screw receiving holes of plate 2. Once the initial bone screws are in place in the vertebrae 50a, the plate holder 100 or 800 may be removed from the plate 2. The compression of the fusion graft construct between the two adjacent vertebrae 50a and 50b is achieved as follows:

Compression post 54 is driven through the central locking hole 12 of plate 2 by means of insertion tool 90, shown in FIGS. 33, 34 and 35, into the vertebral bone of vertebra 50b, where it will be used in a subsequent step to apply a compression force between vertebrae 50a and 50b. Compression post 54 consists of a shaft 56 having a sharp point 57 at its lower end, an enlarged central collar 58 which serves as a depth stop, and a circumferential groove 59 proximate its upper end, defining an enlarged head 55.

Compression post insertion tool 90 consists of a shaft 92 having a closed hollow portion 94 at its lower end 96 for receiving compression post 54 and an enlarged percussion cap 98 at its other end. Compression post insertion tool 90 also includes in its lower end 96 a second opening 95 having a recess 99 in its inside wall for permitting engagement of the enlarged head 55 on the compression post 54 within the depression 97. The second opening 95 is in communication with the hollow portion 94 of the insertion tool 90, as shown in FIG. 35.

Referring to FIG. 38, the bore 132 in the second compression arm 130 of compression tool 100 is then applied over compression post 54 in vertebrae 50b, and the plate engaging element 108 is inserted in the bore 106 of the first compression arm 104 of compression tool 100. The hook 110 of the plate engaging element 108 shown in FIG. 36 is fitted into the notch 18 at the end of the plate 2 which is fixed by the bone screws 30 inserted into the vertebra 50a, as shown in FIG. 38. As indicated above, however, the compression tool 100 can be rotated so that the first compression arm 104 is now at the bottom and is able to fit over the compression post 54 in vertebrae 50c.

Since the plate is attached to vertebrae 50a by means of bone screws 30 and compression post 54 is fixed to the adjacent vertebrae 50b, movement of the first and second compression arms 104 and 130 in the direction of vertebrae 50a by rotation of handle 140 results in compression of the bone graft construct 51 between the adjacent vertebrae 50a and 50b. The distance of several millimeters is sufficient for compression of the bone graft construct 51. Once the desired compression is obtained, bone screw pilot holes can be formed in vertebral body 50b by means of pilot hole forming apparatus 60, as described above, for insertion of bone screws 30 into bone screw receiving holes 8 of bone plate 2, fixing the plate 2 to the adjacent vertebrae 50b. Compression tool 100 can then be withdrawn by activation of the release.

FIG. 39 illustrates the use of compression tool 100 to induce compression between the lower two vertebral bodies 50b and 50c after bone screws 30 have been installed in the middle vertebral body 50b as just described. As shown in FIG. 39, compression post 54 remains in place in the middle vertebral body 50b and an additional compression post 54 is driven into the lower vertebral body 50c by means of pilot hole forming tool 60 distal to the plate itself in the recess between the end projections 4 to allow for the lower compression post 64 to be moved towards vertebrae 50b upwardly as shown. The original compression post 64 is inserted in bore 106 in the first compression arm 104 and the additional compression post 54 is inserted into the bore 132 of the second compression arm 130 of compression tool 100. Again, as discussed above, the turning of the handle 140 results in the two compression arms 104, 130 moving towards one another, resulting in the compression post 54 in vertebrae 50c moving towards the upper compression post 54 in vertebrae 50b, once again compressing the fusion graft construct 51 between vertebrae 50b and 50c. The upper compression post 54 in vertebrae 50b can not move since the vertebrae 50b has been fixed to the plate by the insertion of the bone screws 30 in the bone screw receiving holes 8 of the plate 2. Thus, only the lower compression post 54 and vertebrae 50c can move. As before, the pilot holes associated with vertebrae 50c are formed and the bone screws 30 are inserted through bone screw receiving holes 6. The compression tool 100 is then removed. Compression post 54 is then extracted from the vertebrae by inserting it in the second opening 95 of the compression post insertion/removal tool 90, so that it engages the enlarged head 55 of the end of compression post 54 by depression 97, as shown in FIG. 34.

It is recognized that other variations in the order of compression may be employed. For example, during the compression of the fusion graft construct 51 between vertebrae 50b and 50c, the hook 110 of plate engagement element 108 may engage the notch 18 in the end of the plate 2, and the other compression arm of the compression tool 100 may engage the compression post 54 in the third adjacent vertebrae 50c. It should also be noted that plate 2 has a recess end cut out portion between the lobes at the end of the plate for insertion of the compression post 54 in the vertebrae. Otherwise, there may not be room below the end of the plate 2 for insertion of the compression post 54.

It will be noted that the above-described procedure will be performed with the bone screws 30 fully inserted into vertebral bodies 50a, 50b and 50c and lordosis is maintained during compression of the bone graft construct 51.

As indicated above, the procedure for attaching the plate 2 to the vertebrae 50a, 50b and 50c was illustrated without the locking screws 20, 21 in place on the plate 2. FIG. 40 is a perspective view showing the plate 2 of FIGS. 1–5, at a stage of a surgical procedure when bone screws 30 have been fully installed in three adjacent vertebrae 50a, 50b and 50c, and locking screws 20, 21 have been rotated through an angle of about 90° to lock three bone screws 30 in place; the left-hand locking screw 20 as viewed has been rotated through an angle of about 60° to lock three bone screws 30 in place and the central locking screw 21 has been rotated through an angle of about 90° to lock two other bone screws 30 in place. At this time, one of the camming surfaces 44 of each locking screw 20, 21 rests atop the screw head 32 of a respective bone screw 30.

Installation of the locking cap 300 can also be performed with a tool 220 such as shown in FIGS. 41 and 42 having a suitably shaped tip 222 with a length corresponding to the depth of hole 306 in a locking cap 300. The end 222 of tool 220 is flared just proximal to the most distal end so that it creates a friction fit with the screw cap 300 for ease of manipulation, and prevents the screw cap 300 from falling off the tool 200.

Figure 43:
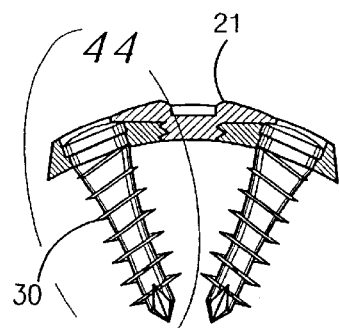
FIG. 43 is a partial cross-sectional view showing a cervical plate, locking element, and bone screws along lines 43—43 of FIG. 40.

FIG. 43 is a cross-sectional view in the plane of the center of the two end locking screw holes 6 of plate 2, with two bone screws 30 in their installed positions and looking element 21 in its locking position. FIG. 44 is an enlarged view of one of the bone screws 30 in plate 2 of FIG. 43. In a preferred embodiment, the axis of each screw 30 is generally perpendicular to tangents to the upper and lower surfaces of plate 2 at points which are intersected by the longitudinal axis of the associated bone screw 30. Thus, because of the curvature of plate 2 in the plane of FIG. 43, bone screws 30 can be directed so as to converge toward one another at a desired angle Preferably, such angle will be greater than 14°. More preferably, such angle will be greater than 14° and less than 30°. The axis of the two bone screws 30 shown in FIG. 43 may subtend an angle of about 45N. Alternatively, the curvature of the plate from side to side may be so as to conform to the surface of the anterior aspect of the human adult cervical spine and the axis of the paired screw hole may deviate from being perpendicular to the plate when viewed on end to achieve optimal convergence.

Because the bone screws 30, once inserted, are locked to the plate, a "claw" of a rigid triangular frame structure is obtained at each pair of bone screws 30 such that the attachment of plate 2 to the vertebral bodies 50a, 50b and 50c would be highly secure due to the trapping of a wedged mass of bone material between the angled bone screws triangle, even if any thread stripping should occur. The "claw" may be further formed by three angled bone screws in a tripod configuration or by four bone screws in a four sided claw configuration.

A plating system according to each of the above embodiments can be installed in the same manner as described above, and using the same instruments and tools, as illustrated and described above with respect to the first embodiment. In the case of the embodiment shown in FIG. 22, the compression operations would be performed by means of slot 232 instead of the middle locking screw hole 12.

b.) The Single Locking Plate Systems

The single locking plate system will now be described. FIGS. 47–52 are views of a first embodiment of a single locking plate system. The contour of plate 600 is the same as the plate 2 shown in FIGS. 1–5. Plate 600 contains bone screw receiving holes 602 which are internally threaded 603 for receiving corresponding locking elements in the form of a locking cap 610, shown in FIGS. 56–59. For example, in plate 600, the bone screw hole 602 has an outer diameter of approximately 5 mm with a preferred range of 4–6 mm; and a threaded inner diameter of approximately 4.8 mm, with a range of 3.5–5.8 mm for this use. Attaching means other than threads may be used, such as bayonet type attachment elements.

The bottom of each bone screw receiving hole 602 has an inwardly stepped portion of properly selected dimensions for retaining an associated bone screw 170, as shown in FIGS. 53–55. As described in greater detail below, in this embodiment, a single locking element in the form of a locking cap 610 having threads 608 shown in FIGS. 56–59, is associated with each of the bone screws receiving holes 602.

The difference between the bone screw 170 used in the single locking embodiment of the plate from the bone screw used in association with the multiple locking plate is essentially due to the fact that whereas in the multiple locking plate embodiment the locking elements slide over a portion of the top 39 of the screw head 32, in the single locking embodiment the locking cap 610 fits over the head 172 of the bone screw 170. Therefore, the head 172 of the bone screw 170 of the present embodiment need not be smooth. This permits the head 172 of this embodiment bone screw 170 to be thicker and stronger.

FIG. 65 shows two bone screws 170 and associated threaded locking caps 610 in their fully installed positions. In these positions, head portions 174 and 176 of each bone screw 170 form an interference fit with corresponding portions of an associated bone screw receiving hole 602. Rim 612 of each threaded locking cap 610 forms an interference fit with upper portion 178 of the head of its associated bone screw 170. Because the thread 608 of each locking cap 610 mates precisely with the internal thread in an associated bone screw receiving hole 602, each threaded locking cap 610 is additionally subjected to a clamping force between associated head portion 178 and the internal threads 603 of associated bone screw receiving!hole 602. The rounded head 614 of each threaded locking cap 610 assures that the upper surface of an assembled plating system will be free of sharp edges, or projections.

Figure 81:
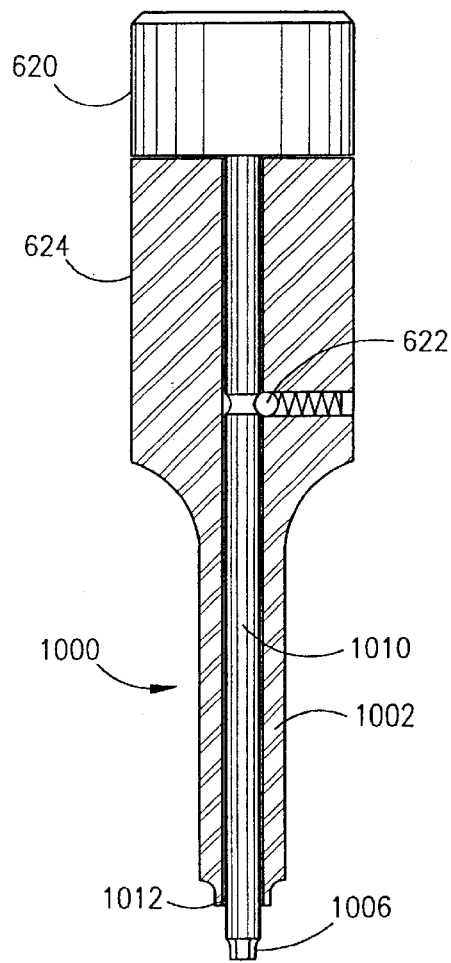
FIG. 81 is a side elevational view of another embodiment of the tool of FIG. 80.

Referring to FIGS. 80 and 81 tools for use in inserting both the bone screws and the locking cap in the single locking plate 600 are shown. In the first embodiment of the driving tool 1000 shown in FIG. 80, the tool 1000 has an outer tubular housing 1002. Within the housing 1002 is a torks type or hexagonal driver 1004 that has a projecting end 1006 that corresponds to the recess 306 in the cap 610 for engagement with the cap 610. As indicated above, the driver 1004 is configured so that it makes a firm attachment for the locking cap 610 for holding the locking cap 610firmly to the driver. The hex driver 1004 is hollow so as to be able to permit the shaft 1010 of a Phillips or torks screw driver to fit through the hollow portion 1012 for engagement by its tip 1012 with the corresponding recess 180 of bone screw 170 for engagement by the end 1006 of the driver 1004. The shaft 1010 of the.driver 1000 is longer than the tubular housing and driver 1004 has an upper end (not shown) extending from the top end of the tubular housing 1002 so that it can be rotated by the handle.

The housing 1002 has a diameter that permits the locking cap 610 to be held within the inner end of the tubular housing 1002 by a friction fit or to the driver 1004. It is appreciated that other methods of holding the locking cap 610 within the end of the tubular housing 1000 may also be employed.

As shown in FIG. 80, the operation of the bone screw and locking element driver 1000 is as follows: the cap 610 is inserted onto the end of the cap driver 1004, and then the cap driver 1004 with the shaft 1010 of the bone screw driver passing through the central longitudinal opening of the cap driver. As shown, the bone screw driver shaft 101 0 passes through the recess 306 in the cap 610 and engages the recess 180 in the head of the bone screw 170. The bone screw 170 is shown being installed in a bone screw receiving hole in the plate 600. The handle (not shown) of the bone screw driver is rotated, thereby screwing the bone screw 170 in place. Since the diameter of the bone screw driver is less than the width of the recess 306 of the cap 610, the bone screw driver shaft 1010 is able to rotate without rotation of the cap 610.

The hollow tubular housing 1002 rests on the top surface of the plate 600 and assists in the alignment of the shaft 1010 in relationship to the plate. Once the bone screw 170 is inserted, the cap driver 1004 is depressed until the threads 608 on the outside of the cap 610 engages the threads 603 of the bone screw receiving hole. The cap driver 1004 is then turned until the cap 610 is securely locked in place.

In FIG. 81, an alternative embodiment of the combination bone screw and locking cap driver is shown. In this embodiment, a housing is not used. Instead, the driver shaft 1010 holds the cap 610 by friction and the handle 620 for the bone screw driver shaft 1010 is rotated. A ball spring assembly 622 holds the cap driver 1002 up until the bone screw has been screwed into the bone screw receiving hole. Driver 1010 has an elongated portion that once the bone screw has been installed, the ball spring 622 is depressed and the handle 624 associated with the cap driver is permitted to descend for rotation of the cap 610. A tubular housing can be employed to assist in aligning of the cap 610 in the bone screw receiving hole, as indicated above.

The drivers shown in FIGS. 80 and 81 simplify the procedure, and reduce the number of instruments that are necessary to be used during the installation procedure. The procedure is quick and reliable, giving the physician more assurance that small watch parts will not be lost or difficult to manipulate.

FIG. 52 is a top view of the plate 600 partially installed, with threaded locking caps 600 installed in bone screw receiving holes 602.

FIGS. 53–55 show a bone screw 170 for use with the single locking plating system according to the invention. Bone screw 170 differs from bone screw 30 previously described in detail, only with regard to the stepped configuration of head 172. Preferably, bone screw 170 includes a lower portion 174 which is contiguous with the screw shank and has a reduced diameter equal to the maximum diameter of the shank 176. Portion 178 of head 172 also has smaller diameter than lower portion 174 The thread 182 has the same configuration as for the bone screw 30 discussed above. However, either embodiment of bone screws can be used with any of the plates.

As in the case of the multiple locking plating system described above, the bone screws 170 for use in the single locking plating system are preferably solid, where the screws adjoin the lower plate surface, where screws used with prior art plates are most prone to breakage, the only recess in the heads being for engagement of the tip 222 of driving tool 220 and with the recess being above the critical area. Therefore, these bone screws 170 remain robust. The screw heads are not deeply slitted into portions and the locking caps do not impose a radial outer force on the associated bone screw heads so the screw heads do not spread apart so as to be stressed and weakened.

Figure 71:
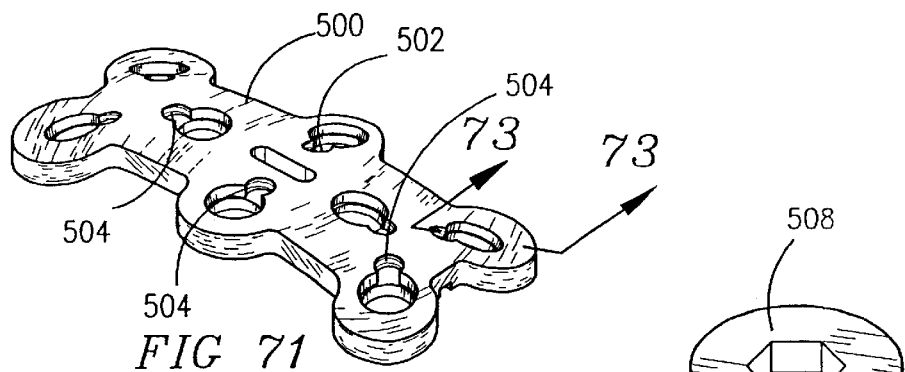
FIG. 71 is a top perspective view of a second embodiment of a cervical single locking plate having individual locking elements to lock each bone screw.
Figure 73:
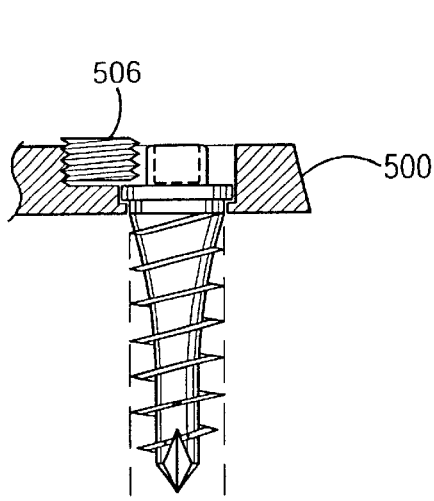
FIG. 73 is a partial side sectional view of the plate of FIG. 71 viewed along lines 73—73 with the locking element of FIG. 72 in place to hold a bone screw, but not fully tightened.
Figure 75:
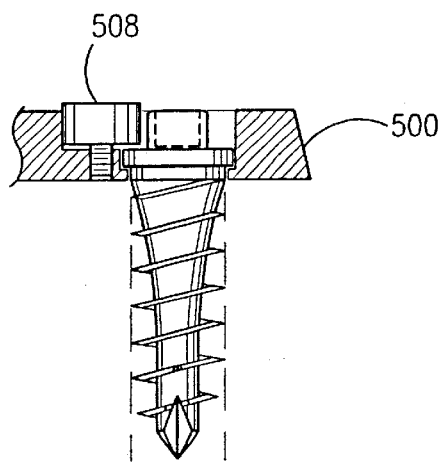
FIG. 75 is a side sectional view of the first modification of the plate of FIG. 71 with the locking element of FIG. 74.
Figure 76:
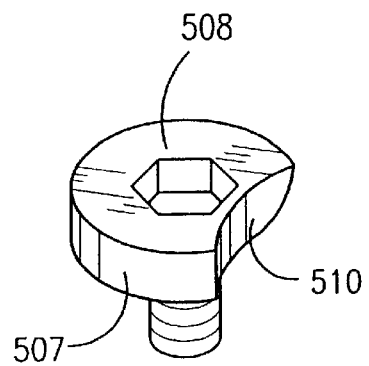
FIG. 76 is a perspective view of an alternative locking element for use with the first modification of the plate of FIG. 71.
Figure 78:
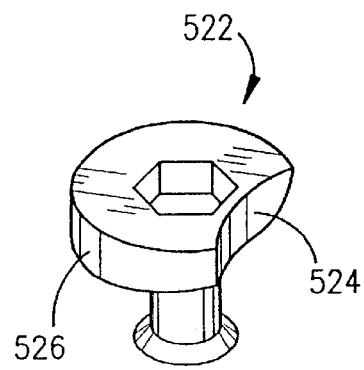
FIG. 78 is a top perspective view of another alternative locking element in the form of a rivet for use with a second modification of the locking plate of FIG. 71.
Figure 77:
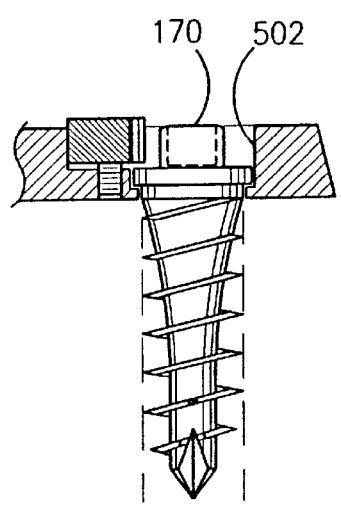
FIG. 77 is a partial side sectional view of the first modification of the plate of FIG. 71 with the locking element of FIG. 76 in place.
Figure 79:
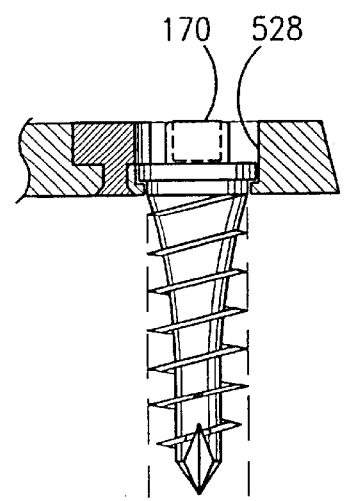
FIG. 79 is a partial side sectional detail view of the plate of FIG. 71 modified to use a locking element of FIG. 78 shown in place.

Referring to FIGS. 71, 73 and 75 another alternative embodiment of the single locking plate system of the present invention is shown and referred to by the number 500. The plate 500 has the same contour as the plate 2 shown in FIGS.

Figure 74:
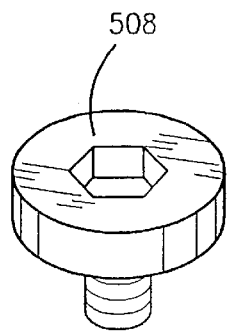
FIG. 74 is a top perspective view of an alternative locking element for use with a first modification of the cervical single locking plate of FIG. 71.
Figure 72:
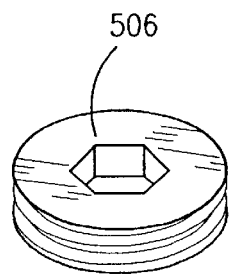
FIG. 72 is a top perspective view of a threaded locking element for use with the cervical single locking plate of FIG. 71

1–5, but associated with each of the bone screw openings 502, are threaded openings 524 offset from the bone screw openings 502 for receiving the locking element 506, 508, shown in FIGS. 72 and 74 as a threaded locking set screw or cap 506 or screw 508.

Figure 82:
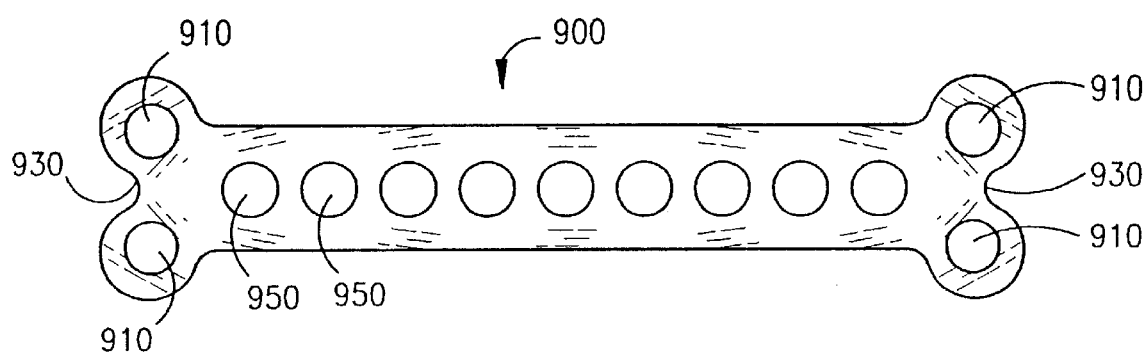

It is appreciated that other configurations of single locking plates may be employed. Referring to FIG. 82, a single locking plate 900 is shown in which there are a pair of bone screw receiving holes 910 at its ends 930 and a number of bone screw receiving holes 950 along the longitudinal axis of the plate 900. The additional bone screw receiving holes 950 permit a single plate to be able to be aligned with a number of different sized vertebrae disc spaces, and bone fusion grafts. As indicated above, the plate of the present invention shown in FIGS. 1–5, requires that a properly sized plate be selected by the surgeon so that each pair of bone screw receiving holes 6, 8 line up with the appropriate vertebrae. This requires a number of different sized plates to be available for optimum attachment of the bone screw receiving holes to each of the vertebrae. With the plate 900 of FIG. 82, the close spacing and increased number of central openings permit the surgeon to locate at least one appropriate opening to be aligned with each of the intermediate vertebrae, and/or bone grafts.

The procedure for installation of the single locking plates is substantially the same as described herein in detail for the multiple locking plates. The central longitudinal slot 670 in the single locking plates is used for the compression procedure. The same instrumentation is used to create the plate hole either by means of a punch or a drill. FIGS. 60–69 show the various steps in the procedure for installation of the single locking plates, comparable to the steps employed in the installation of the multiple locking plates.

Referring to FIGS. 76–79 the heads 507 and 526 of the locking elements 508 and 522 have a recess 510 and 524 corresponding to the radius of the bone screw openings 502 and 528 so that the locking element 508 and 522 may be installed in place prior to the insertion of the bone screw 170 into the bone screw receiving hole 502 and 528. When the locking elements 508 and 522 are rotated, a portion of its head extends over the top of the head of bone screw 170 to lock it in place. As with the above embodiments, the bottom surface of the locking screws 508 and 522 can have a camming or other configuration for engagement with the top surface 39 of the associated bone screw 170.

While the plate instrumentation and method have been described in association with attaching a plate to the vertebrae of the spine, it should be appreciated that the plates can be adopted for specification to other parts of the body. See, for example, application Ser. No. 09/022,344, filed Feb. 11, 1998, and titled Skeletal Plating System, now U.S. Pat. No. 6,139,550, incorporated by reference above. However, the dimensions of the plate, the specific contours and placement of the bone screw receiving holes would have to be modified.

Similarly, the bone screws described in this application could be used in other parts of the.body, again being modified so as to serve their intended purposed, depending on the size of the body part in which they are to be installed.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

While specific innovative features may have been presented in reference to specific examples, they are just examples, and it should be understood that various combinations of these innovative features beyond those specifically shown are taught such that they may now be easily alternatively combined and are hereby anticipated and claimed.

What is claimed is:

1. A plating system, comprising:
an anterior cervical plate adapted to be applied to the anterior human cervical spine, said plate having a lower surface adapted to contact the anterior aspect of at least one cervical vertebral body and an upper surface opposite said lower surface, at least one bone screw receiving hole extending from said upper surface through said lower surface, said bone screw receiving hole being adapted to receive at least one bone screw for engaging the cervical vertebral body to attach said plate to the cervical spine; and
a bone screw adapted to attach said plate to the cervical vertebral body, said bone screw comprising:
a head adapted to block further forward motion of said screw through said bone screw receiving hole of said plate;
a tip for insertion into the cervical vertebral body;
a shaft between said tip and said head, said shaft having a mid-longitudinal axis and a root diameter at transverse cross sections along the mid-longitudinal axis, said shaft having a first shaft portion proximate said tip and a second shaft portion proximate said head, the root diameter of said first shaft portion being less than the root diameter of said second shaft portion; and
a thread along at least a portion of said shaft adapted to engage the cervical vertebral body, said thread having an outer diameter that is generally uniform along at least a substantial portion of each of said first and second shaft portions, said thread having a pitch, said pitch along at least a portion of the length of said first shaft portion being substantially the same as said pitch along at least a portion of the length of said second shaft portion, said thread having opposed side faces angled relative to each other to form a base at said root diameter of said shaft, said base being smaller proximate said second shaft portion than proximate said first shaft portion, said screw being made of a material suitable for implantation into the human skeleton.

2. The plating system of claim 1, wherein said root diameter of said shaft is curved along at least a portion of the length of said shaft in a direction between said head and said tip along the mid-longitudinal axis of said shaft.

3. The plating system of claim 2, wherein said root diameter of said shaft is at least a portion of a concave curve.

4. The plating system of claim 1, wherein said root diameter increases along a portion of said shaft in a direction from said tip toward said head of said screw.

5. The plating system of claim 4, wherein the rate of increase of said root diameter is greater proximate said head of said screw.

6. The plating system of claim 1, wherein said second shaft portion has a generally circular cross section.

7. The plating system of claim 1, wherein said second shaft portion is generally conical.

8. The plating system of claim 1, wherein said first shaft portion has a generally circular cross section.

9. The plating system of claim 1, wherein said first shaft portion is generally cylindrical.

10. The plating system of claim 1, wherein said tip is at least one of pointed, tapered, and coned.

11. The plating system of claim 1, wherein said tip is configured to be self-tapping.

12. The plating system of claim 11, wherein said tip includes at least one of a pointed tip, cutting flutes, and decreased thread height.

13. The plating system of claim 1, wherein said tip includes cutting flutes that interrupt at least one turn of said thread proximate said tip.

14. The plating system of claim 1, wherein said outer diameter of said thread diminishes proximate said tip.

15. The plating system of claim 1, wherein said thread has a maximum outer diameter in the range of 3.6 mm to 5.2 mm.

16. The plating system of claim 1, wherein said thread pitch is in the range of 1.25 to 2.5 mm.

17. The plating system of claim 1, wherein said thread has opposed side faces being angled relative to each other to form an apex of said thread, said side faces forming an included angle in the range of 11 degrees to 30 degrees.

18. The plating system of claim 1, wherein said thread has opposed side faces, said side faces being angled relative to each other to form a base at said root diameter of said shaft and a crest opposite said base, said side faces having a thickness therebetween in the range of 0.25 mm to 0.60 mm at said base.

19. The plating system of claim 11, wherein said screw has an overall length in the range of 10 mm to 22 mm.

20. The plating system of claim 1, wherein said head has a maximum root diameter no greater than the maximum root diameter of said shaft.

21. The plating system of claim 11, wherein said head has a top surface that is at least in part curved.

22. The plating system of claim 1, wherein said head has a length parallel to the mid-longitudinal axis of said shaft in the range of 1 mm to 3 mm.

23. The plating system of claim 1, wherein said head has a diameter in the range of 3.8 mm to 6 mm.

24. The plating system of claim 1, wherein at least a portion of said plating system comprises at least in part of one of bone and bone growth promoting material.

25. The plating system of claim 24, wherein said bone growth promoting material is selected from one of bone, bone derived products, bone morphogenetic protein, and hydroxyapatite.

26. The plating system of claim 1, in combination with a bone growth promoting material.

27. The plating system of claim 26, wherein said bone growth promoting material is selected from one of bone, bone derived products, bone morphogenetic protein, and hydroxyapatite.

28. The plating system of claim 1, wherein at least a portion of said plating system is treated with a bone growth promoting substance.

29. The plating system of claim 1, wherein at least a portion of said plating system is at least in part resorbable.

30. The plating system of claim 1, wherein at least a portion of said plating system is formed of a porous material.

31. The plating system of claim 1, wherein at least a portion of said plating system is treated to promote bone ingrowth between said plate and the adjacent vertebral bodies.

32. A plating system, comprising:
an anterior cervical plate adapted to be applied to the anterior human cervical spine, said plate having a lower surface adapted to contact the anterior aspect of at least one cervical vertebral body and an upper surface opposite said lower surface, at least one bone screw receiving hole extending from said upper surface through said lower surface, said bone screw receiving hole being adapted to receive at least one bone screw for engaging the cervical vertebral body to attach said plate to the cervical spine; and
a bone screw adapted to attach said plate to the cervical vertebral body, said bone screw comprising:
a head adapted to block further forward motion of said screw through said bone screw receiving hole of said plate;
a tip for insertion into the cervical vertebral body;
shaft between said tip and said head, said shaft having a mid-longitudinal axis and a root diameter at transverse cross sections along the mid-longitudinal axis, said shaft having a first shaft portion proximate said tip and a second shaft portion proximate said head, the root diameter of said first shaft portion being less than the root diameter of said second shaft portion; and
a thread along at least a portion of said shaft adapted to engage the cervical vertebral body, said thread having an outer diameter that is generally uniform along at least a substantial portion of each of said first and second shaft portions, said thread having a profile with opposed side faces and a crest, said crest along at least a portion, of the length of said first shaft portion being substantially uniform to said crest along at least a portion of the length of said second shaft portion proximate said head, said screw being made of a material suitable for implantation into the human skeleton.

33. The plating system of claim 32, wherein said root diameter of said shaft is curved along at least a portion of the length of said shaft in a direction between said head and said tip along the mid-longitudinal axis of said shaft.

34. The plating system of claim 33, wherein said root diameter of said shaft is at least a portion of a concave curve.

35. The plating system of claim 32, wherein said root diameter increases along a portion of said shaft in a direction from said tip toward said head of said screw.

36. The plating system of claim 35, wherein the rate of increase of said root diameter is greater proximate said head of said screw.

37. The plating system of claim 32, wherein said second shaft portion has a generally circular cross section.

38. The plating system of claim 32, wherein said second shaft portion is generally conical.

39. The plating system of claim 32, wherein said first shaft portion has a generally circular cross section.

40. The plating system of claim 32, wherein said first shaft portion is generally cylindrical.

41. The plating system of claim 32, wherein said tip is at least one of pointed, tapered, and coned.

42. The plating system of claim 32, wherein said tip is configured to be self-tapping.

43. The plating system of claim 42, wherein said tip includes at least one of a pointed tip, cutting flutes, and decreased thread height.

44. The plating system of claim 32, wherein said tip includes cutting flutes that interrupt at least one turn of said thread proximate said tip.

45. The plating system of claim 32, wherein said outer diameter of said thread diminishes proximate said tip.

46. The plating system of claim 32, wherein said thread has a maximum outer diameter in the range of 3.6 mm to 5.2 mm.

47. The plating system of claim 32, wherein said thread has a pitch in the range of 1.25 to 2.5 mm.

48. The plating system of claim 32, wherein said opposed side faces are angled relative to each other to form an apex of said thread said side faces forming an included angle in the range of 11 degrees to 30 degrees.

49. The plating system of claim 32, wherein said opposed side faces are angled relative to each other to form a base at said root diameter of said shaft and said crest being opposite said base, said side faces having a thickness therebetween in the range of 0.25 mm to 0.60 mm at said base.

50. The plating system of claim 32, wherein said screw has an overall length in the range of 10 mm to 22 mm.

51. The plating system of claim 32, wherein said head has a maximum root diameter no greater than the maximum root diameter of said shaft.

52. The plating system of claim 32, wherein said head has a top surface that is at least in part curved.

53. The plating system of claim 32, wherein said head has a length parallel to the mid-longitudinal axis of said shaft in the range of 1 mm to 3 mm.

54. The plating system of claim 32, wherein said head has a diameter in the range of 3.8 mm to 6 mm.

55. The plating system of claim 32, wherein at least a portion of said plating system comprises at least in part of one of bone and bone growth promoting material.

56. The plating system of claim 55, wherein said bone growth promoting material is selected from one of bone, bone derived products, bone morphogenetic protein, and hydroxyapatite.

57. The plating system of claim 32, in combination with a bone growth promoting material.

58. The plating system of claim 57, wherein said bone growth promoting material is selected from one of bone, bone derived products, bone morphogenetic protein, and hydroxyapatite.

59. The plating system of claim 32, wherein at least a portion of said plating system is treated with a bone growth promoting substance.

60. The plating system of claim 32, wherein at least a portion of said plating system is at least in part resorbable.

61. The plating system of claim 32, wherein at least a portion of said plating system is formed of a porous material.

62. The plating system of claim 32, wherein at least a portion of said plating system is treated to promote bone ingrowth between said plate and the adjacent vertebral bodies.

63. A plating system, comprising:
   an anterior cervical plate adapted to be applied to the anterior human cervical spine, said plate having a lower surface adapted to contact the anterior aspect of at least one cervical vertebral body and an upper surface opposite said lower surface, at least one bone screw receiving hole extending from said upper surface through said lower surface, said bone screw receiving hole being adapted to receive at least one bone screw for engaging the cervical vertebral body to attach said plate to the cervical spine; and
   a bone screw adapted to attach said plate to the cervical vertebral body, said bone screw comprising:
      a head adapted to block further forward motion of said screw through said bone screw receiving hole of said plate;
      a tip for insertion into the cervical vertebral body;
      a shaft between said tip and said head, said shaft having a mid-longitudinal axis and a root diameter at transverse cross sections along the mid-longitudinal axis, said shaft having a first shaft portion proximate said tip and a second shaft portion proximate said head, the root diameter of said first shaft portion being less than the root diameter of said second shaft portion; and
      a thread along at least a portion of said shaft adapted to engage the cervical vertebral body, said thread having an outer diameter that is generally uniform along at least a substantial portion of each of said first and second shaft portions, said thread having opposed side faces intersecting at an angle to form a crest along at least a portion of the length of said second shaft portion proximate said head, said thread having a pitch, said pitch along at least a portion of the length of said first shaft portion being substantially the same as said pitch along at least a portion of the length of said second shaft portion, said screw being made of a material suitable for implantation into the human skeleton.

64. The plating system of claim 63, wherein said root diameter of said shaft is curved along at least a portion of the length of said shaft in a direction between said head and said tip along the mid-longitudinal axis of said shaft.

65. The plating system of claim 64, wherein said root diameter of said shaft is at least a portion of a concave curve.

66. The plating system of claim 63, wherein said root diameter increases along a portion of said shaft in a direction from said tip toward said head of said screw.

67. The plating system of claim 66, wherein the rate of increase of said root diameter is greater proximate said head of said screw.

68. The plating system of claim 63, wherein said second shaft portion has a generally circular cross section.

69. The plating system of claim 63, wherein said second shaft portion is generally conical.

70. The plating system of claim 63, wherein said first shaft portion has a generally circular cross section.

71. The plating system of claim 63, wherein said first shaft portion is generally cylindrical.

72. The plating system of claim 63, wherein said tip is at least one of pointed, tapered, and coned.

73. The plating system of claim 63, wherein said tip is configured to be self-tapping.

74. The plating system of claim 73, wherein said tip includes at least one of a pointed tip, cutting flutes, and decreased thread height.

75. The plating system of claim 63, wherein said tip includes cutting flutes that interrupt at least one turn of said thread proximate said tip.

76. The plating system of claim 63, wherein said outer diameter of said thread diminishes proximate said tip.

77. The plating system of claim 63, wherein said thread has a maximum outer diameter in the range of 3.6 mm to 5.2 mm.

78. The plating system of claim 63, wherein said thread pitch is in the range of 1.25 to 2.5 mm.

79. The plating system of claim 63, wherein said opposed side faces are angled relative to each other to form an apex of said thread, said side faces forming an included angle in the range of 11 degrees to 30 degrees.

80. The plating system of claim 63, wherein said opposed side faces are angled relative to each other to form a base at said root diameter of said shaft and said crest being opposite said base, said side faces having a thickness therebetween in the range of 0.25 mm to 0.60 mm at said base.

81. The plating system of claim 63, wherein said screw has an overall length in the range of 10 mm to 22 mm.

82. The plating system of claim 63, wherein said head has a maximum root diameter no greater than the maximum root diameter of said shaft.

83. The plating system of claim 63, wherein said head has a top surface that is at least in part curved.

84. The plating system of claim 63, wherein said head has a length parallel to the mid-longitudinal axis of said shaft in the range of 1 mm to 3 mm.

85. The plating system of claim 63, wherein said head has a diameter in the range of 3.8 mm to 6 mm.

86. The plating system of claim 63, wherein at least a portion of said plating system comprises at least in part of one of bone and bone growth promoting material.

87. The plating system of claim 86, wherein said bone growth promoting material is selected from one of bone, bone derived products, bone morphogenetic protein, and hydroxyapatite.

88. The plating system of claim 63, in combination with a bone growth promoting material.

89. The plating system of claim 88, wherein said bone growth promoting material is selected from one of bone, bone derived products, bone morphogenetic protein, and hydroxyapatite.

90. The plating system of claim 63, wherein at least a portion of said plating system is treated with a bone growth promoting substance.

91. The plating system of claim 63, wherein at least a portion of said plating system is at least in part resorbable.

92. The plating system of claim 63, wherein at least a portion of said plating system is formed of a porous material.

93. The plating system of claim 63, wherein at least a portion of said plating system is treated to promote bone ingrowth between said plate and the adjacent vertebral bodies.

94. Plating system, comprising:
an anterior cervical plate adapted to be applied to the anterior human cervical spine, said plate having a lower surface adapted to contact the anterior aspect of at least one cervical vertebral body and an upper surface opposite said lower surface, at least one bone screw receiving hole extending from said upper surface through said lower surface, said bone screw receiving hole being adapted to receive at least one bone screw for engaging the cervical vertebral body to attach said plate to the cervical spine; and
a bone screw adapted to attach said plate to the cervical vertebral body, said bone screw comprising:
a head adapted to block further forward motion of said screw through said bone screw receiving hole of said plate;
a tip for insertion into the cervical vertebral body;
a shaft between said tip and said head, said shaft having a mid-longitudinal axis and a root diameter at transverse cross sections along the mid-longitudinal axis, said root diameter of said shaft being curved along at least a portion of the length of said shaft in a direction between said head and said tip along the mid-longitudinal axis of said shaft, said shaft having a first shaft portion proximate said tip and a second shaft portion proximate said head, the root diameter of said first shaft portion being less than the root diameter of said second shaft portion; and
a thread along at least a portion of said shaft adapted to engage the cervical vertebral body, said thread having an outer diameter that is generally uniform along at least a substantial portion of each of said first and second shaft portions, said screw being made of a material suitable for implantation into the human skeleton.

95. The plating system of claim 94, wherein said root diameter of said shaft is at least a portion of a concave curve.

96. The plating system of claim 94, wherein said root diameter increases along a portion of said shaft in a direction from said tip toward said head of said screw.

97. The plating system of claim 96, wherein the rate of increase of said root diameter is greater proximate said head of said screw.

98. The plating system of claim 94, wherein said second shaft portion has a generally circular cross section.

99. The plating system of claim 94, wherein said second shaft portion is generally conical.

100. The plating system of claim 94, wherein said first shaft portion has a generally circular cross section.

101. The plating system of claim 94, wherein said first shaft portion is generally cylindrical.

102. The plating system of claim 94, wherein said tip is at least one of pointed, tapered, and coned.

103. The plating system of claim 94, wherein said tip is configured to be self-tapping.

104. The plating system of claim 103, wherein said tip includes at least one of a pointed tip, cutting flutes, and decreased thread height.

105. The plating system of claim 94, wherein said tip includes cutting flutes that interrupt at least one turn of said thread proximate said tip.

106. The plating system of claim 94, wherein said outer diameter of said thread diminishes proximate said tip.

107. The plating system of claim 94, wherein said thread has a maximum outer diameter in the range of 3.6 mm to 5.2 mm.

108. The plating system of claim 94, wherein said thread has a pitch in the range of 1.25 to 2.5 mm.

109. The plating system of claim 94, wherein said thread has opposed side faces being angled relative to each other to form an apex of said thread, said side faces forming an included angle in the range of 11 degrees to 30 degrees.

110. The plating system of claim 94, wherein said thread has opposed side faces, said side faces being angled relative to each other to form a base at said root diameter of said shaft and a crest opposite said base, said side faces having a thickness therebetween in the range of 0.25 mm to 0.60 mm at said base.

111. The plating system of claim 94, wherein said screw has an overall length in the range of 10 mm to 22 mm.

112. The plating system of claim 94, wherein said head has a maximum root diameter no greater than the maximum root diameter of said shaft.

113. The plating system of claim 94, wherein said head has a top surface that is at least in part curved.

114. The plating system of claim 94, wherein said head has a length parallel to the mid-longitudinal axis of said shaft in the range of 1 mm to 3 mm.

115. The plating system of claim 94, wherein said head has a diameter in the range of 3.8 mm to 6 mm.

116. The plating system of claim 94, wherein at least a portion of said plating system comprises at least in part of one of bone and bone growth promoting material.

117. The plating system of claim 116, wherein said bone growth promoting material is selected from one of bone, bone derived products, bone morphogenetic protein, and hydroxyapatite.

118. The plating system of claim 94, in combination with a bone growth promoting material.

119. The plating system of claim 118, wherein said bone growth promoting material is selected from one of bone, bone derived products, bone morphogenetic protein, and hydroxyapatite.

120. The plating system of claim 94, wherein at least a portion of said plating system is treated with a bone growth promoting a substance.

121. The plating system of claim 94, wherein at least a portion of said plating system is at least in part resorbable.

122. The plating system of claim 94, wherein at least a portion of said plating system is formed of a porous material.

123. The plating system of claim 94, wherein at least a portion of said plating system is treated to promote bone ingrowth between said plate and the adjacent vertebral bodies.

124. Plating system, comprising:
- an anterior cervical plate adapted to be applied to the anterior human cervical spine, said plate having a lower surface adapted to contact the anterior aspect of at least one cervical vertebral body and an upper surface opposite said lower surface, at least one bone screw receiving hole extending from said upper surface through said lower surface, said bone screw receiving hole being adapted to receive at least one bone screw for engaging the cervical vertebral body to attach said plate to the cervical spine; and
- a bone screw adapted to attach said plate to the cervical vertebral body, said bone screw comprising:
  - a shaft having a leading end configured to pass at least in part through said plate and adapted for Insertion into the bone of a cervical vertebral body and a trailing end opposite said leading end, said shaft having a mid-longitudinal axis and a root diameter at transverse cross sections along the mid-longitudinal axis; and
  - a thread having a length along at least a portion of said shaft, said thread adapted to engage the bone of the vertebral body, said thread having opposed side faces being angled relative to each other to form an apex of said thread, said side faces forming an included angle in the range of 11 degrees to 30 degrees along said thread length, said screw being made of a material suitable for human implantation.

125. The plating system of claim 124, wherein said root diameter of said shaft is curved along at least a portion of the length of said shaft in a direction between said leading end and said trailing end along the mid-longitudinal axis of said shaft.

126. The plating system of claim 125, wherein said root diameter of said shaft is at least a portion of a concave curve.

127. The plating system of claim 125, wherein said root diameter increases along a portion of said shaft in a direction from said leading end toward said trailing end.

128. The plating system of claim 127, wherein the rate of increase of said root diameter is greater proximate said trailing end.

129. The plating system of claim 124, wherein said shaft has a first shaft portion proximate said leading end and a second shaft portion proximate said trailing end, said second shaft portion having a generally circular cross section.

130. The plating system of claim 124, wherein said shaft has a first shaft portion proximate said leading end and a second shaft portion proximate said trailing end, said second shaft portion being generally conical.

131. The plating system of claim 124, wherein said shaft has a first shaft portion proximate said leading end and a second shaft portion proximate said trailing end, said first shaft portion having a generally circular cross section.

132. The plating system of claim 124, wherein said shaft has a first shaft portion proximate said leading end and a second shaft portion proximate said trailing end, said first shaft portion being generally cylindrical.

133. The plating system of claim 124, wherein said leading end includes a tip that is at least one of pointed, tapered, and coned.

134. The plating system of claim 124, wherein said leading end includes a tip that is configured to be self-tapping.

135. The plating system of claim 134, wherein said tip includes at least one of a pointed tip, cutting flutes, and decreased thread height.

136. The plating system of claim 124, wherein said leading end of said screw has a tip with cutting flutes that interrupt at least one turn of said thread proximate said tip.

137. The plating system of claim 124, wherein said thread has an outer diameter that diminishes proximate said leading end.

138. The plating system of claim 124, wherein said thread has a maximum outer diameter in the range of 3.6 mm to 5.2 mm.

139. The plating system of claim 124, wherein said thread has a pitch in the range of 1.25 to 2.5 mm.

140. The plating system of claim 124, wherein said opposed side faces are angled relative to each other to form a base at said root diameter of said shaft and a crest opposite said base, said side faces having a thickness therebetween in the range of 0.25 mm to 0.60 mm at said base.

141. The plating system of claim 124, wherein said screw has an overall length in the range of 10 mm to 22 mm.

142. The plating system of claim 124, further comprising a head adapted to block further forward motion of said screw through said bone screw receiving hole of said plate.

143. The plating system of claim 142, wherein said head has a maximum root diameter no greater than the maximum root diameter of said shaft.

144. The plating system of claim 142, wherein said head has a top surface that is at least in part curved.

145. The plating system of claim 142, wherein said head has a length parallel to the mid-longitudinal axis of said shaft in the range of 1 mm to 3 mm.

146. The plating system of claim 142, wherein said head has a diameter in the range of 3.8 mm to 6 mm.

147. The plating system of claim 124, wherein at least a portion of said plating system comprises at least in part of one of bone and bone growth promoting material.

148. The plating system of claim 147, wherein said bone growth promoting material is selected from one of bone, bone derived products, bone morphogenetic protein, and hydroxyapatite.

149. The plating system of claim 124, in combination with a bone growth promoting material.

150. The plating system of claim 149, wherein said bone growth promoting material is selected from one of bone, bone derived products, bone morphogenetic protein, and hydroxyapatite.

151. The plating system of claim 124, wherein at least a portion of said plating system is treated with a bone growth promoting substance.

152. The plating system of claim 124, wherein at least a portion of said plating system is at least in part resorbable.

153. The plating system of claim 124, wherein at least a portion of said plating system is formed of a porous material.

154. The plating system of claim 124, wherein at least a portion of said plating system is treated to promote bone ingrowth between said plate and the adjacent vertebral bodies.

155. A plating system, comprising:
- an anterior cervical plate adapted to be applied to the anterior human cervical spine, said plate having a lower surface adapted to contact the anterior aspect of at least one cervical vertebral body and an upper surface opposite said lower surface, at least one bone screw receiving hole extending from said upper surface through said lower surface, said bone screw receiving hole being adapted to receive at least one bone screw for engaging the cervical vertebral body to attach said plate to the cervical spine; and a bone screw adapted to attach said plate to the cervical vertebral body, said bone screw comprising:

a shaft having a leading end configured to pass at least in part through said plate and adapted for insertion into the bone of a cervical vertebral body, a mid-longitudinal axis, and a trailing end opposite said leading end, said shaft having a root diameter at transverse cross sections along the mid-longitudinal axis; and a thread along at least a portion of said shaft, said thread adapted to engage the bone of the cervical vertebral body, said thread having opposed side faces, said side faces being angled relative to each other to form a base at said root diameter of said shaft and a crest opposite said base, said side faces having at least three different base thicknesses therebetween in the range of 0.25 mm to 0.60 mm at said base, said screw being made of a material suitable for human implantation.

156. The plating system of claim 155, wherein said root diameter of said shaft is curved along at least a portion of the length of said shaft in a direction between said leading end and said trailing end along the mid-longitudinal axis of said shaft.

157. The plating system of claim 156, wherein said root diameter of said shaft is at least a portion of a concave curve.

158. The plating system of claim 155, wherein said root diameter increases along a portion of said shaft in a direction from said leading end toward said trailing end.

159. The plating system of claim 158, wherein the rate of increase of said root diameter is greater proximate said trailing end.

160. The plating system of claim 155, wherein said shaft has a first shaft portion proximate said leading end and a second shaft portion proximate said trailing end, said second shaft portion having a generally circular cross section.

161. The plating system of claim 155, wherein said shaft has a first shaft portion proximate said leading end and a second shaft portion proximate said trailing end, said second shaft portion being generally conical.

162. The plating system of claim 155, wherein said shaft has a first shaft portion proximate said leading end and a second shaft portion proximate said trailing end, said first shaft portion having a generally circular cross section.

163. The plating system of claim 155, wherein said shaft has a first shaft portion proximate said leading end and a second shaft portion proximate said trailing end, said first shaft portion being generally cylindrical.

164. The plating system of claim 155, wherein said leading end includes a tip that is at least one of pointed, tapered, and coned.

165. The plating system of claim 155, wherein said leading end includes a tip that is configured to be self-tapping.

166. The plating system of claim 165, wherein said tip includes least one of a pointed tip, cutting flutes, and decreased thread height.

167. The plating system of claim 155, wherein said leading end of said screw has a tip with cutting flutes that interrupt at least one turn of said thread proximate said tip.

168. The plating system of claim 155, wherein said thread has an outer diameter that diminishes proximate said leading end.

169. The plating system of claim 155, wherein said thread has a maximum outer diameter in the range of 3.6 mm to 5.2 mm.

170. The plating system of claim 155, wherein said thread has a pitch in the range of 1.25 to 2.5 mm.

171. The plating system of claim 155, wherein said opposed side faces are angled relative to each other to form an apex of said thread, said side faces forming an included angle in the range of 11 degrees to 30 degrees.

172. The plating system of claim 155, wherein said screw has an overall length in the range of 10 mm to 22 mm.

173. The plating system of claim 155, further comprising a head adapted to block further forward motion of said screw through said bone screw receiving hole of said plate.

174. The plating system of claim 155, wherein said head has a maximum root diameter no greater than the maximum root diameter of said shaft.

175. The plating system of claim 155, wherein said head has a top surface that is at least in part curved.

176. The plating system of claim 155, wherein said head has a length parallel to the mid-longitudinal axis of said shaft in the angle of 1 mm to 3 mm.

177. The plating system of claim 155, wherein said head has a diameter in the range of 3.8 mm to 6 mm.

178. The plating system of claim 155, wherein at least a portion of said plating system comprises at least in part of one of bone and bone growth promoting material.

179. The plating system of claim 178, wherein said bone growth promoting material is selected from one of bone, bone derived products, bone morphogenetic protein, and hydroxyapatite.

180. The plating system of claim 155, in combination with a bone growth promoting material.

181. The plating system of claim 180, wherein said bone growth promoting material is selected from one of bone, bone derived products, bone morphogenetic protein, and hydroxyapatite.

182. The plating system of claim 155, wherein at least a portion of said plating system is treated with a bone growth promoting substance.

183. The plating system of claim 155, wherein at least a portion of said plating system is at least in part resorbable.

184. The plating system of claim 155, wherein at least a portion of said plating system is formed of a porous material.

185. The plating system of claim 155, wherein at least a portion of said plating system is treated to promote bone ingrowth between said plate and the adjacent vertebral bodies.

186. A plating system, comprising:

an anterior cervical plate adapted to be applied to the anterior human cervical spine, said plate having a lower surface adapted to contact the anterior aspect of at least one cervical vertebral body and an upper surface opposite said lower surface, at least one bone screw receiving hole extending from said upper surface through said lower surface, said bone screw receiving hole being adapted to receive at least one bone screw for engaging the cervical vertebral body to attach said plate to the cervical spine; and a bone screw adapted to attach said plate to the cervical vertebral body, said bone screw comprising:

a leading end configured to pass at least in part through said plate and adapted for insertion into the bone of the cervical vertebral body, a mid-longitudinal axis, and a trailing end opposite said leading end, a portion of said screw proximate said trailing end being configured to contact said plate and to prevent said screw from passing entirely through said plate;

a shaft between said leading end and said trailing end, said shaft having a root diameter that increases along a substantial portion of the mid-longitudinal axis of said screw in a direction from said leading end toward said trailing end; and a thread along said shaft adapted to engage the bone of the vertebral body, said thread having an outer diameter that is generally uniform along a substantial portion of said shaft, said thread having opposed side faces, said side faces being angled relative to each other to form the apex of said thread, said side faces forming an included angle in the range of 11 degrees to 21 degrees, said side faces forming a base at said root diameter of said shaft, said side faces having a thickness therebetween in the range of 0.25 mm to 0.60 mm at said base, said screw being made of a material suitable for human implantation.

187. The plating system of claim 186, wherein said root diameter of said shaft is curved along at least a portion of the length of said shaft in a direction between said leading end and said trailing end along the mid-longitudinal axis of said shaft.

188. The plating system of claim 187, wherein said root diameter of said shaft is at least a portion of a concave curve.

189. The plating system of claim 186, wherein the rate of increase of said root diameter is greater proximate said trailing end of said screw.

190. The plating system of claim 186, wherein said shaft has a first shaft portion proximate said leading end and a second shaft portion proximate said trailing end, said second shaft portion having a generally circular cross section.

191. The plating system of claim 186, wherein said shaft has a first shaft portion proximate said leading end and a second shaft portion proximate said trailing end, said second shaft portion being generally conical.

192. The plating system of claim 186, wherein said shaft has a first shaft portion proximate said leading end and a second shaft portion proximate said trailing end, said first shaft portion having a generally circular cross section.

193. The plating system of claim 186, wherein said shaft has a first shaft portion proximate said leading end and a second shaft portion proximate said trailing end, said first shaft portion being generally cylindrical.

194. The plating system of claim 186, wherein said leading end of said screw includes a tip that is at least one of pointed, tapered, and coned.

195. The plating system of claim 186, wherein said leading end of said screw includes a tip that is configured to be self-tapping.

196. The plating system of claim 186, wherein said tip includes at least one of a pointed tip, cutting flutes, and decreased thread height.

197. The plating system of claim 186, wherein said leading end of said screw has a tip with cutting flutes that interrupt at least one turn of said thread proximate said tip.

198. The plating system of claim 186, wherein said outer diameter of said thread diminishes proximate said leading end.

199. The plating system of claim 186, wherein said thread has a maximum outer diameter in the range of 3.6 mm to 5.2 mm.

200. The plating system of claim 186, wherein said thread has a pitch in the range of 1.25 to 2.5 mm.

201. The plating system of claim 186, wherein said screw has an overall length in the range of 10 mm to 22 mm.

202. The plating system of claim 186, further comprising a head adapted to block further forward motion of said screw through said bone screw receiving hole of said plate.

203. The plating system of claim 202, wherein said head has a maximum root diameter no greater than the maximum root diameter of said shaft.

204. The plating system of claim 202, wherein said head has a top surface that is at least in part curved.

205. The plating system of claim 202, wherein said head has a length parallel to the mid-longitudinal axis of said screw in the range of 1 mm to 3 mm.

206. The plating system of claim 202, wherein said head has a diameter in the range of 3.8 mm to 6 mm.

207. The plating system of claim 202, wherein at least a portion of said plating system comprises at least in part of one of bone and bone growth promoting material.

208. The plating system of claim 207, wherein said bone growth promoting material is selected from one of bone, bone derived products, bone morphogenetic protein, and hydroxyapatite.

209. The plating system of claim 186, in combination with a bone growth promoting material.

210. The plating system of claim 209, wherein said bone growth promoting material is selected from one of bone, bone derived products, bone morphogenetic protein, and hydroxyapatite.

211. The plating system of claim 186, wherein at least a portion of said plating system is treated with a bone growth promoting substance.

212. The plating system of claim 186, wherein at least a portion of said plating system is at least in part resorbable.

213. The plating system of claim 186, wherein at least a portion of said plating system is formed of a porous material.

214. The plating system of claim 186, wherein at least a portion of said plating system is treated to promote bone ingrowth between said plate and the adjacent vertebral bodies.

215. A plating system comprising:

an anterior cervical plate adapted to be applied to the anterior human cervical spine, said plate having a lower surface adapted to contact the anterior aspect of at least one cervical vertebral body and an upper surface opposite said lower surface, at least one bone screw receiving hole extending from said upper surface through said lower surface, said bone screw receiving hole being adapted to receive at least one bone screw for engaging the cervical vertebral body to attach said plate to the cervical spine; and a bone screw adapted to attach said plate to the cervical vertebral body, said bone screw comprising:

a tip;

a head having a length in the range of 1 mm to 3 mm and a diameter in the range of 3.8 mm to 7.0 mm;

a shaft having a maximum root diameter in the range of 3.6 mm to 5.2 mm, said root diameter of said shaft being tapered from proximately below said head along the longitudinal axis of said shaft to proximately above said tip, said shaft having a length in the range of 10 mm to 22 mm; and a thread on said shaft having a pitch in the range of 1.25 mm to 2.5 mm with a sharp and thin profile, said thread having two faces angled relative to each other to form an apex having an angle in the range of 11 degrees to 21 degrees, said thread having a base that is in the range of 0.25 to 0.6 mm thick, said thread having an outer diameter that is generally constant along a substantial portion of the length of said shaft.

216. The plating system of claim 215, wherein said root diameter of said shaft is curved along at least a portion of the length of said shaft in a direction between said head and said tip along the longitudinal axis of said shaft.

217. The plating system of claim 216, wherein said root diameter of said shaft is at least a portion of a concave curve.

218. The plating system of claim 215, wherein said root diameter increases along a portion of said shaft in a direction from said tip toward said head of said screw.

219. The plating system of claim 215, wherein the rate of increase of said root diameter is greater proximate said head of said screw.

220. The plating system of claim 215, wherein said shaft has a first shaft portion proximate said tip and a second shaft portion proximate said head, said second shaft portion having a generally circular cross section.

221. The plating system of claim 215, wherein said shaft has a first shaft portion proximate said tip and a second shaft portion proximate said head, said second shaft portion being generally conical.

222. The plating system of claim 215, wherein said shaft has a first shaft portion proximate said tip and a second shaft portion proximate said head, said first shaft portion having a generally circular cross section.

223. The plating system of claim 215, wherein said shaft has a first shaft portion proximate said tip and a second shaft portion proximate said head, said first shaft portion being generally cylindrical.

224. The plating system of claim 215, wherein said tip is at least one of pointed, tapered, and coned.

225. The plating system of claim 215, wherein said tip is configured to be self-tapping.

226. The plating system of claim 215, wherein said tip includes at least one of a pointed tip, cutting flutes, and decreased thread height.

227. The plating system of claim 215, wherein said tip includes cutting flutes that interrupt at least one turn of said thread proximate said tip.

228. The plating system of claim 215, wherein said outer diameter of said thread diminishes proximate said tip.

229. The plating system of claim 215, wherein said thread has a maximum outer diameter in the range of 3.6 mm to 5.2 mm.

230. The plating system of claim 215, wherein said head has a maximum root diameter no greater than the maximum root diameter of said shaft.

231. The plating system of claim 215, wherein said head has a top surface that is at least in part curved.

232. The plating system of claim 215, wherein at least a portion of said plating system comprises at least in part of one of bone and bone growth promoting material.

233. The plating system of claim 215, wherein said bone growth promoting material is selected from one of bone, bone derive products, bone morphogenetic protein, and hydroxyapatite.

234. The plating system of claim 215, in combination with a bone growth promoting material.

235. The plating system of claim 234, wherein said bone growth promoting material is selected from one of bone, bone derived products, bone morphogenetic protein, and hydroxyapatite.

236. The plating system of claim 215, wherein at least a portion of said plating system is treated with a bone growth promoting substance.

237. The plating system of claim 215, wherein at least a portion of said plating system is at least in part resorbable.

238. The plating system of claim 215, wherein at least a portion of said plating system is formed of a porous material.

239. The plating system of claim 215, wherein at least a portion of said plating system is treated to promote bone ingrowth between said plate and the adjacent vertebral bodies.

* * * * *

UNITED STATES PATENT AND TRADEMARK OFFICE
CERTIFICATE OF CORRECTION

PATENT NO. : 6,620,163 B1
DATED : September 16, 2003
INVENTOR(S) : Gary Karlin Michelson, M.D.

It is certified that error appears in the above-identified patent and that said Letters Patent is hereby corrected as shown below:

Column 31,
Lines 28 and 33, change "11" to -- 1 --.

Column 32,
Line 14, before "shaft" (first occurrence) insert -- a --.

Column 33,
Line 5, change "thread" to -- thread, --.

Column 35,
Line 35, change "Plating" to -- A plating --.

Column 37,
Line 12, change "Plating" to -- A plating --.
Line 26, change "Insertion" to -- insertion --.

Column 41,
Line 54, change "186" to -- 195 --.

Column 42,
Line 16, change "202" to -- 186 --.

Column 43,
Line 12, change "215" to -- 218 --; and
Line 35, change "215" to -- 225 --.

UNITED STATES PATENT AND TRADEMARK OFFICE
CERTIFICATE OF CORRECTION

PATENT NO.   : 6,620,163 B1
DATED        : September 16, 2003
INVENTOR(S)  : Gary Karlin Michelson, M.D.

It is certified that error appears in the above-identified patent and that said Letters Patent is hereby corrected as shown below:

Column 44,
Line 17, change "215" to -- 232 --.

Signed and Sealed this

Twenty-third Day of November, 2004

JON W. DUDAS
*Director of the United States Patent and Trademark Office*